US012640234B2

(12) United States Patent
Dhapola et al.

(10) Patent No.: US 12,640,234 B2
(45) Date of Patent: May 26, 2026

(54) METHOD AND SYSTEM FOR SUBSAMPLING OF CELLS FROM SINGLE-CELL GENOMICS DATASET

(71) Applicant: NYGEN ANALYTICS AB, Lund (SE)

(72) Inventors: Parashar Dhapola, Lund (SE); Göran Karlsson, Lund (SE)

(73) Assignee: NYGEN ANALYTICS AB, Lund (SE)

( * ) Notice: Subject to any disclaimer, the term of this patent is extended or adjusted under 35 U.S.C. 154(b) by 508 days.

(21) Appl. No.: 18/025,951

(22) PCT Filed: Sep. 15, 2021

(86) PCT No.: PCT/EP2021/075306
§ 371 (c)(1),
(2) Date: Mar. 13, 2023

(87) PCT Pub. No.: WO2022/058339
PCT Pub. Date: Mar. 24, 2022

(65) Prior Publication Data
US 2023/0352119 A1      Nov. 2, 2023

(30) Foreign Application Priority Data
Sep. 15, 2020    (SE) .................................... 2051077-2

(51) Int. Cl.
*G16B 30/00*          (2019.01)
*G16B 30/20*          (2019.01)
(Continued)

(52) U.S. Cl.
CPC ............. *G16B 30/20* (2019.02); *G16B 45/00* (2019.02); *G16B 50/20* (2019.02)

(58) Field of Classification Search
None
See application file for complete search history.

(56) References Cited

U.S. PATENT DOCUMENTS

2020/0020419 A1    1/2020   Kahvejian et al.
2020/0265917 A1    8/2020   Khurana et al.

FOREIGN PATENT DOCUMENTS

CA            3072273 A1 *  12/2019   ........... C12Q 1/6806
WO      WO 2017027559 A1     2/2017
WO      WO 2019/243969       * 12/2019   ............. G16B 45/00

OTHER PUBLICATIONS

Florian Klimm. Functional module detection through integration of single-cell RNA sequencing data with protein-protein interaction networks. BMC Genomics. Nov. 2020.*

(Continued)

*Primary Examiner* — Tuankhanh D Phan
(74) *Attorney, Agent, or Firm* — MOSER TABOADA

(57)          ABSTRACT

The present disclosure relates to a computer-implemented method of extracting a subsample of cells from a plurality of cells in a single-cell genomics dataset, the method comprising the steps of: obtaining a single-cell genomics dataset represented in at least two dimensions, wherein information about each cell is represented in a first dimension and information about genomic features is represented in a second dimension; generating a cell-cell neighborhood graph from the single-cell genomics dataset, the cell-cell neighborhood graph providing information about similarities of the genomic features of the cells, wherein the cells are represented as vertices in the cell-cell neighborhood graph; dividing the cells in the cell-cell neighborhood graph into seed cells and non-seed cells; assigning at least one first prize to the seed cells and at least one second prize to the non-seed cells in the cell-cell neighborhood graph; and traversing the cell-cell neighborhood graph using a prize collecting steiner tree algorithm to obtain a subsample of cells. The present disclosure further relates to a computer (Continued)

100 system for extracting a subsample of cells from a plurality of cells in a single-cell genomics dataset.

19 Claims, 14 Drawing Sheets

(51) Int. Cl.
  *G16B 45/00*          (2019.01)
  *G16B 50/20*          (2019.01)

(56)               References Cited

OTHER PUBLICATIONS

Swedish Search Report for Patent Application No. 2051077-2 dated May 6, 2021.

International Search Report for PCT/EP2021/075306 dated Dec. 22, 2021.

International Preliminary Report on Patentability for PCT/EP2021/075306 dated Dec. 21, 2022.

Klimm et al., Functional module detection through integration of single-cell RNA sequencing data with protein-protein interaction networks, BMC Genomics, Nov. 2, 2020, p. 1-10. 10p, vol. 21 Issue 1, https://doi.org/10.1186/s12864-020-07144-2.

Akhmedov et al., A prize-collecting Steiner tree application for signature selection to stratify diffuse large B-cell lymphoma subtypes, bioRxiv, Feb. 26, 2018, pp. 1-15, https://doi.org/10.1101/272294.

Akhmedov et al., A Fast Prize-Collecting Steiner Forest Algorithm for Functional Analyses in Biological Networks, ICIAP: International Conference on Image Analysis and Processing, 17th International Conference, Naples Italy, Sep. 13, 2012, p. 263-276 DOI: 10.1007/978-3-319-59776-8 22.

Liu et al., VariFunNet, an integrated multiscale modeling framework to study the effects of rare non-coding variants in Genome-Wide Association Studies: applied to Alzheimer's Disease, 2017 IEEE International Conference on Bioinformatics and Biomedicine (BIBM), Nov. 13, 2017, p. 2177-2182, doi: 10.1109/BIBM.2017.8217995.

Klimm et al., Functional module detection through integration of single-cell RNA sequencing data with protein-protein interaction networks, bioRxiv, Sep. 2, 2019, pp. 1-18, DOI: 10.1101/698647, https://www.biorxiv.org/content/10.1101/698647v2.full.pdf.

Klimm et al., Functional module detection through integration of single-cell RNA sequencing data with protein-protein interaction networks—Supplementary Information, biorxiv, Jul. 10, 2019, pp. 1-15, URL:https://www.biorxiv.org/content/biorxiv/early/2019/09/02/698647/DC1/embed/media-1.pdf?download=true.

Parahar et al., Scarf: A toolkit for memory efficient analysis of large-scale single cell genomics data, bioRxiv, May 3, 2021, DOI: 10.1101/2021.05.02.441899, URL:https://www.biorxiv.org/content/10.1101/2021.05.02.441899v1.full.pdf.

Luecken et al., Current best practices in single-cell RNA-seq analysis: a tutorial, Molecular Systems Biology, Jun. 1, 2019, p. 8746, vol. 15, No. 6, XP055924251, GB, ISSN:1744-4292, DOI: 10.15252/msb.20188746, URL:https://www.ncbi.nlm.nih.gov/pmc/articles/PMC6582955/pdf/MSB-15-e8746.pdf.

Parashardhapola:               scarf/datastore.py            at 3751abb0b3dbbf29cb123e4b6e1afa23ac735579.parashardhapola/scarf. GitHub, Sep. 10, 2020, XP055960888, URL:https://github.com/parashardhapola/scarf/blob/3751abb0b3dbbf29cb123e4b6e1afa23ac735579/scarf/datastore.py.

Anoymous, GitHub log file for repository Scarf, Apr. 29, 2021, XP093005028.

Hie et al., Geometric Sketching Compactly Summarizes the Single-Cell Transcriptomic Landscape, HHS Public Access, Jun. 5, 2019, pp. 483-493.e7, vol. 8, No. 6, XP055870045, US, ISSN:2405-4712, DOI:10.1016/j.cels.2019.05.003.

\* cited by examiner

100

Obtaining a single-cell
genomics dataset
101

Generating cell-cell
neighborhoood graph 102

Dividing cells in the cell-
cell neighborhood graph
into seed cells and non-
seed cells        103

Traversing the cell-cell
neighborhood graph using
a prize collecting steiner
tree
104

300

300

300

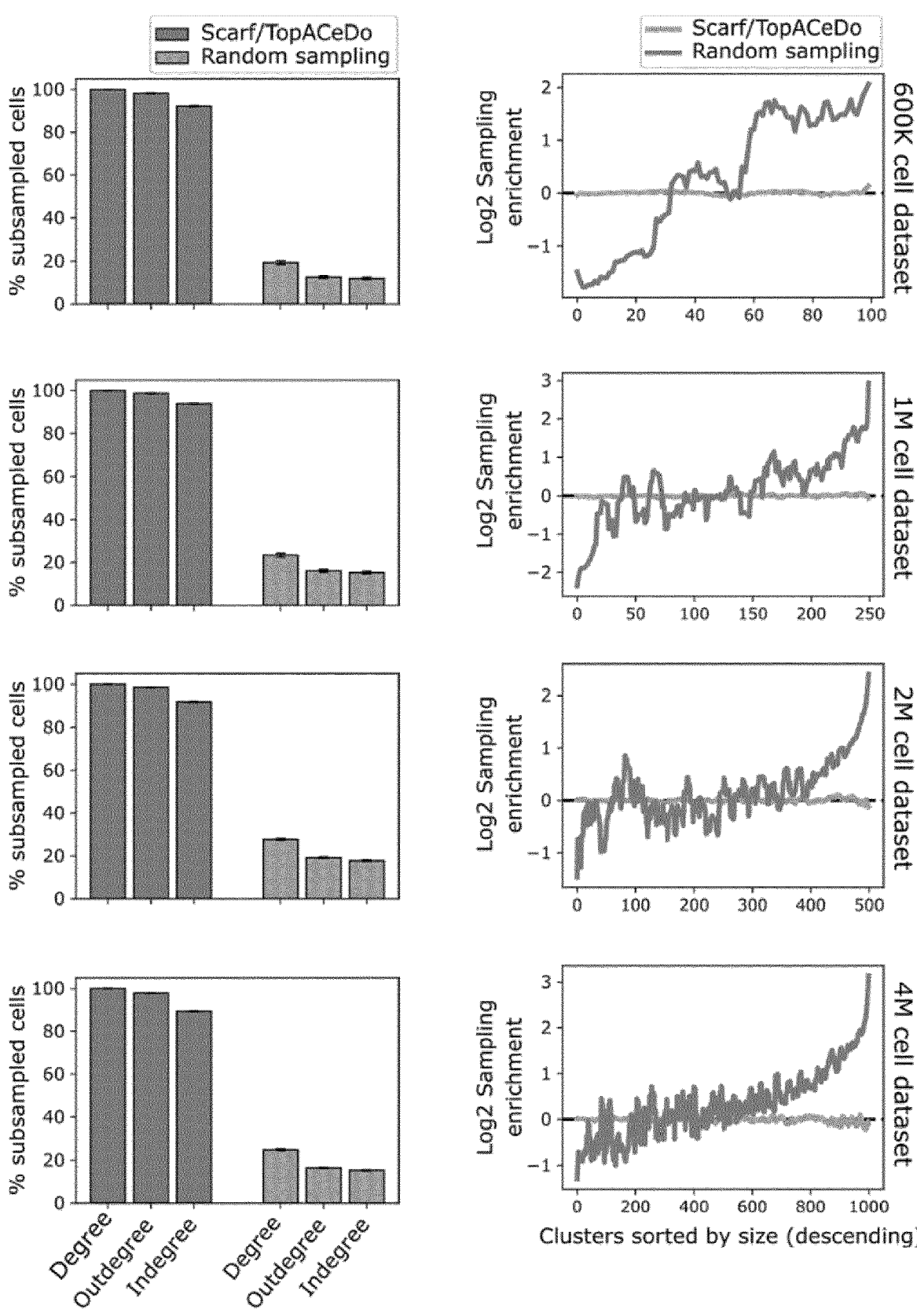
FIG. 12                    FIG. 13

METHOD AND SYSTEM FOR SUBSAMPLING OF CELLS FROM SINGLE-CELL GENOMICS DATASET

The present disclosure relates to a computer-implemented method and system of extracting a subsample of cells from a plurality of cells in a single-cell genomics dataset. The disclosed method outlines a stepwise process that allows subsampling of cells from large-scale single-cell genomics datasets with high memory efficiency.

BACKGROUND

Single-cell DNA genome sequencing involves isolating a single cell, amplifying the whole genome or region of interest, constructing sequencing libraries, and then applying next-generation DNA sequencing. In mammalian systems, single-cell DNA sequencing has been widely applied to study normal physiology and disease.

A single-cell genomics assay can be targeted to determine the presence of nucleotide variants in the genome, estimate number of RNA molecules for each transcribed gene, identify open regions of DNA in the chromatin, identify epigenetic marks on chromatin, etc. Multiple methods and protocols exist to achieve this but they all invariantly generate a large number of sequenced fragments of nucleotide sequences in such a way that each sequence can be ascribed its cell of origin.

Numerous computer-implemented methods have been developed to process and analyze such sequences from single-cell sequencing in order to obtain a count matrix. The count matrices are typically two-dimensional tables in which each row contains information about each cell and each column contains information on each genomic feature, or vice-versa. An example of such a two-dimensional table is shown in FIG. 1. Quantified features could be, for example, number of cut sites in each identified accessible region (in the case of single-cell ATAC sequencing), number of complementary DNA (cDNA) fragments for each gene (in the case of the single-cell RNA sequencing) etc.

Typical for single-cell datasets is that they contain a large degree of redundancy in the sense that clusters of cells are of the same cell type and similar to each other. For common analyses aims, such as cell-type specification and heterogeneity analysis this redundancy in the single-cell datasets causes unnecessary data processing time and often necessitates a requirement for large-scale computing infrastructure. This challenge becomes even more pronounced with large single-cell datasets or where a user tries to analyze multiple single-cell datasets as an aggregate.

As single-cell genomics moves towards the generation of data of previously unanalyzable magnitudes, it will be necessary to reduce the single-cell datasets. A frequently applied, and straightforward, solution to do this is to randomly sample cells from the large original single-cell dataset. However, this solution results in suboptimal sample results since it typically fails to represent the manifold of the single-cell dataset in an optimal way. In other existing methods for data sampling, data is either not selected in an optimal way and/or the processing does not make use of the memory of the computer in an efficient way.

There is thus a need for an improved and efficient solution of de-scaling of large-scale single-cell genomics datasets that is computationally efficient and has minimal loss of information.

SUMMARY

One objective of the present disclosure is to provide a technical implementation that is capable of down-sampling single-cell genomics datasets to smaller datasets by selecting a subsample of cells. Preferably, the solution is fully embeddable in readily available computing devices, such as laptop computers. One objective of the present disclosure is to perform data subsampling that preserves the original manifold of the original single-cell genomics dataset.

The method may be applied to single-cell genomics datasets represented as a two-dimensional matrix comprising quantified features of each single cell that was assayed. As can be seen in the example of FIG. 1, information about the cells $(C_1-C_n)$, for example an identification, such as a barcode, is provided in a first dimension, whereas information about genomic features $(F_1-F_n)$ of each cell is represented in a second dimension. As would be recognized by a person skilled in the art, the genomic features may themselves be considered multi-dimensional in the sense that each genomic feature may be considered as a dimension of its own. However, the use of 'first' and 'second' dimension within the context of the present disclosure refers to the first and second dimensions of the matrix representing the single-cell genomics dataset.

A first aspect of the present disclosure relates to a computer-implemented method of extracting a subsample of cells from a plurality of cells in a single-cell genomics dataset. The method comprises the steps of:

obtaining a single-cell genomics dataset represented in at least two dimensions, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph;

dividing the cells in the cell-cell neighborhood graph into seed cells and non-seed cells;

assigning at least one first prize to the seed cells and at least one second prize to the non-seed cells in the cell-cell neighborhood graph; and traversing the cell-cell neighborhood graph using a prize collecting steiner tree algorithm to obtain a subsample of cells.

The single-cell genomics dataset may be obtained by a single-cell genomics sequencing process.

The implementation of the above steps has several advantages. It may allow users with limited computing resources and memory resources to process all the single-cell genomics dataset and then work with a meaningful subsample of cells, or forward the results to a further application. It can drastically reduce the need of memory for large datasets while preserving the original diversity and data manifold. The obtained subsample of cells may capture the full spectrum of information present in the original single-cell genomics dataset. The solution can be used and integrated in an existing workflow or used as a standalone module. A 'manifold', which is a term that generally would be understood by a person skilled in the art in the field of single-cell genomics, can be thought of as a high-dimensional surface. Multiple natural processes generate samples that lie on high dimensional surfaces also known as manifolds. Single cells genomics datasets have few hundreds to hundreds of thousands of features but the biological processes that underlie cellular state are simpler and can be represented in a fewer dimensions. Due to this reasoning, manifold learning is popular in single-cell genomics because the cells can be conceptualized to be lying on an unknown manifold that can be represented using fewer dimensions. A graph representation of single-cell data represents a manifold and sampling on this graph is akin to sampling on the data manifold.

The information about genomic features in the second dimension of the dimension may comprise quantified genomic features, such as an annotated gene, and/or a genomic location in coordinate form of a genomic assembly, and/or a number of cut sites in an identified accessible region, and/or a number of cDNA fragments for each gene. The single-cell genomics dataset may be, but is not limited to, a single-cell RNA-Seq dataset or a single-cell ATAC-Seq dataset.

The steps of the method are further explained and exemplified in the below detailed description. The step of generating the cell-cell neighborhood graph from the single-cell genomics dataset may be implemented using a k nearest neighbors algorithm. The step of dividing the cells in the cell-cell neighborhood graph into seed cells and non-seed cells may be done by clustering and selection but is not limited to these methods. The aim of the step of dividing the cells in the cell-cell neighborhood graph into seed cells and non-seed cells is to prepare data for the step of assigning prizes to the seed cells and non-seed cells in the cell-cell neighborhood graph and traversing the cell-cell neighborhood graph using a prize collecting steiner tree algorithm (POST) to obtain a subsample of cells.

In another aspect, the present disclosure further relates to a computer system comprising:

a memory; and a processing unit configured to perform the steps of:

loading a single-cell genomics dataset represented in at least two dimensions into the memory, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph;

dividing the cells in the cell-cell neighborhood graph into seed cells and non-seed cells;

assigning at least one first prize to the seed cells and at least one second prize to the non-seed cells in the cell-cell neighborhood graph; and traversing the cell-cell neighborhood graph using a prize collecting steiner tree algorithm to obtain a subsample of cells.

The invention further relates to a computer program having instructions, which, when executed by a computing device or computing system, cause the computing device or system to carry out any embodiment of the presently disclosed method of extracting a subsample of cells from a plurality of cells in a single-cell genomics dataset. Computer program in this context shall be construed broadly and include, for example, a computer program to be run on a PC, single board computer or system on chip, or even a mobile phone or tablet, or a computer program adapted to run as part of a software platform.

BRIEF DESCRIPTION OF DRAWINGS

The invention will in the following be described with reference to the accompanying drawings, which are exemplary and not limiting to the presently disclosed method and system of extracting a subsample of cells from a plurality of cells in a single-cell genomics dataset.

FIG. 12 shows a comparison of degree of connections subsampled cells between the present method and random sampling.

FIG. 13 show size of clusters after subsampling.

DETAILED DESCRIPTION

Figure 1:
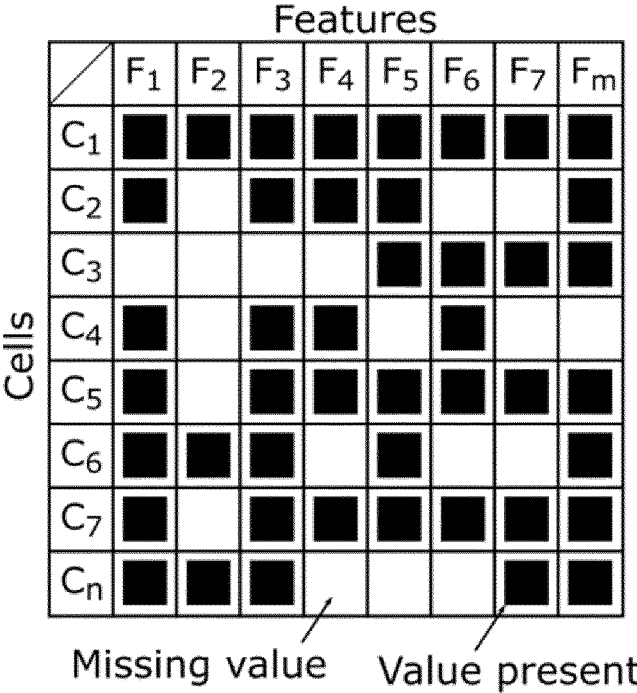
FIG. 1 shows an example of a single-cell genomics dataset represented in two dimensions in a matrix.

Recent advances in the techniques for isolating single cells, together with methods for amplifying their genetic material, make it possible to explore the genomes, such as chromatin, RNA, and DNA of single cells. This field is known as single-cell genomics. In contrast to bulk sequencing, in which gene expression levels that are average expression profiles of individual cells are use, single cell sequencing preserves the information about the cell of origin for each molecule measured. Due to the heterogeneity in cell populations, analyzing a single cell makes it possible to discover mechanisms not seen when studying a bulk population of cells. Single-cell sequencing can characterize individual cells at the molecular level.

Single-cell genomics data can from a wide variety of techniques including but not limited to those that aim to profile and quantity gene expression (scRNA-Seq, SMART-Seq, sciRNA-Seq, Drop-Seq, InDrop), chromatin accessibility (scATAC-Seq, sciATAC-Seq), surface (CITE-Seq, DAB-Seq) or/and in-cell proteome (PEA), methylated regions of DNA (scBS-Seq, sci-MET), modification of DNA bound histones (CutNTag, CutNRun), or any combinations of these modalities. Most of these laboratory protocols involve capture of individual cells from an organism's tissue of interest. Once captured the cells or their extracted nuclei are tagged with unique barcodes such that origin of each molecule (DNA/cDNA fragment) can be traced back to the cell of origin. Most commercial instruments today, use water-in-oil droplets in a microfluidic setup to capture cells/nuclei. The barcoded molecules are pooled and sequenced using next-generation sequencing methods, typically based on one of Illumina's sequencing by synthesis platforms. Once the fragments are sequenced or are in process of being sequenced, the identified sequence of DNA nucleotides is saved in a digital medium. This digital medium eventually stores the information of the sequenced fragments.

The size of single-cell genomics datasets is inherently large as single-cell genomics datasets may comprise millions of cells and a large number of features. For example, single-cell ATAC-Seq datasets can have up to 500,000 features, or even 1,000,000 features. New datasets are being generated at rapid pace due to increasing efficiency and cost effectiveness of single cell sequencing technologies. Due to the large amount of insights they provide, these datasets are not just being generated in a research field but are now being increasingly incorporated in medical diagnostics and pharmaceutical industry. However, the existing analytics platform for these datasets lag behind the pace of data generation.

Large scale single cell genomics datasets like single-cell DNA sequencing, single-cell RNA sequencing, single-cell ATAC sequencing require large computing infrastructure. The requirement for such infrastructure and the accompanying cost of IT management adds substantial amount of cost in order to get actionable meaning out of these datasets.

In the context of the present disclosure, the term 'cells' does not refer to physical cells but to a digital representation of the cells. For example, the cells may be associated with sequenced barcodes. Features of a cell may refer to a certain function, property or characteristic of a cell. In single-cell genomics sequencing, the data analysis steps may include the identification of valid cell barcodes and alignment of sequenced reads to the genome of the organism wherefrom the cells were derived. The aligned sequenced reads are then processed by analytics methods, the choice of which depends on the type of single-cell genomics method used. For example, in the case of single-cell RNA-Seq, the immediate step after alignment is to perform gene quantification. Irrespective of the single-cell genomics method used, the objective of these early steps of analyses is to generate a matrix or a matrix like data structure wherein cells and captured features of cells form the two axes of the matrix. A cell-feature matrix may be a cell-gene or cell-transcript matrix in the case of the single-cell RNA-Seq data. In the case of single-cell ATAC-Seq data, the cell-feature matrix may take the form of a cell-peak matrix.

The present disclosure relates to a method of extracting a subsample of cells from a plurality of cells in a single-cell genomics dataset in a computationally and memory efficient manner, wherein the subsample of cells removes or reduces redundancy and provides a subsample of cells that is representative of the single-cell genomics dataset.

The method may comprise a first step of loading the single-cell genomics dataset into a computer memory in partitions fitting the memory. This may involve converting data from text formats such as CSV (comma separated file) and MTX (Matrix Market exchange format) into a format where data can be loaded efficiently into memory in partitions. Disk-based data persistence formats may be used for this purpose. The objective of these formats is to allow loading of any part of matrix or matrix like datasets into memory. Such disk based formats are implemented through various software libraries, for example, HDF5, Zarr, Apache Arrow, etc.

As provided above, the obtained single-cell genomics dataset may be represented in at least two dimensions, wherein information about each cell is represented in a first dimension and information about genomic features is represented in a second dimension. The information about genomic features in the second dimension may comprise quantified genomic features, such as an annotated gene, and/or a genomic location in coordinate form of a genomic assembly, and/or a number of cut sites in an identified accessible region, and/or a number of cDNA fragments for each gene.

The method may further comprise the step of generating a cell-cell neighborhood graph from the single-cell genomics dataset, the cell-cell neighborhood graph providing information about similarities of the genomic features of the cells, wherein the cells are represented as vertices in the cell-cell neighborhood graph. This step may involve performing a k nearest neighbors algorithm, wherein k nearest neighbors of each cell are identified, wherein the cells are represented as vertices and the vertices are connected via edges if at least one of the vertices is a k nearest neighbor of the other one. The similary of genomic features of the cells may be quantified in various ways. According to one example, the similarity between two cells is inversely proportional to the distances between the cells in the graph. The distance between any pair of cells of cells can be calculated using any suitable distance metric. For example, in the case of Euclidean metric, the distance between a cell, C1 and another cell C2 with each having 1 to N features is computed as:

$$D_{C1-C2} = \sqrt{\sum_{f=1}^{N_f}(C1_f - C2_f)^2}$$

Angular metrics such cosine distances are also often used as they are scale-invariant can be useful when the range of values very different across the cells (usually due to sequencing depth or because cells were pooled from two or more separate experiments.

The method may further comprise the step of dividing the cells in the cell-cell neighborhood graph into seed cells and non-seed cells. This step can be performed by, for example, any suitable clustering method.

The inventors have found that once cells have been divided into seed cells and non-seed cells, traversing the cell-cell neighborhood graph using a prize collecting steiner tree (POST) algorithm to obtain a subsample of cells has been a particularly efficient way of obtaining a useful subsample of cells. In order to successfully apply POST algorithm, the seed cells and non-seed cells are assigned different prizes. Different approaches for assigning the prizes exist. Typically, the seed cells are assigned a high value, or several individual high values, wherein the non-seed cells are assigned a low value, or several individual low values. The values may be between zero and one, and a high value may be, for example, above 0.5, and a low value may be, for example, below 0.5.

Figure 2:
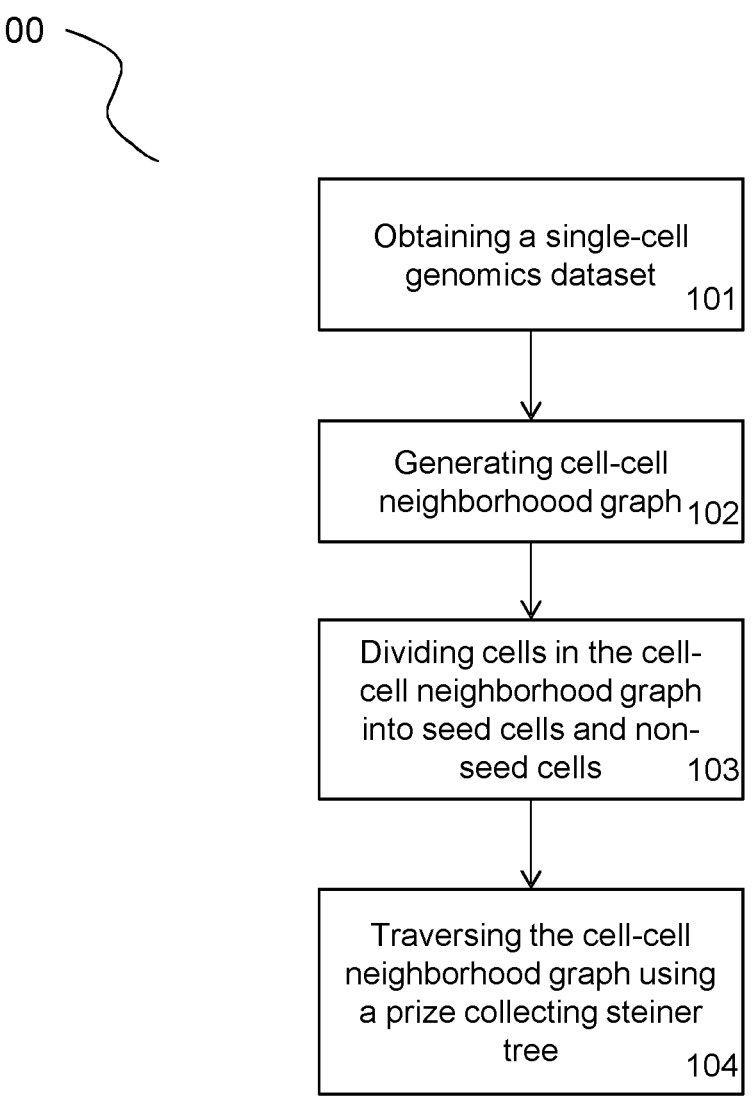
FIG. 2 shows a flow chart of one embodiment of the presently disclosed method of extracting a subsample of cells from a plurality of cells in a single-cell genomics dataset.

FIG. 2 discloses an example of the presently disclosed method (1) of extracting a subsample of cells from a plurality of cells in a single-cell genomics. According to the example the method (100) comprises the steps of:

obtaining a single-cell genomics dataset represented in at least two dimensions, wherein information about each cell is represented in a first dimension and information about genomic features is represented in a second dimension; (101)

generating a cell-cell neighborhood graph from the single-cell genomics dataset, the cell-cell neighborhood graph providing information about similarities of the genomic features of the cells, wherein the cells are represented as vertices in the cell-cell neighborhood graph; (102)

dividing the cells in the cell-cell neighborhood graph into seed cells and non-seed cells; (103)

assigning at least one first prize to the seed cells and at least one second prize to the non-seed cells in the cell-cell neighborhood graph; and traversing the cell-cell neighborhood graph using a prize collecting steiner tree algorithm (POST) to obtain a subsample of cells. (104)

The steps of the presently disclosed method of extracting a subsample of cells from a plurality of cells in a single-cell genomics dataset will in the following be described in greater detail. As would be acknowledged by a person skilled in the art, not all steps may be necessary to carry out the invention. Some of the steps may be optional.

Data Preprocessing

The analysis process of sequenced fragments may begin with conversion of the data to FASTQ data format which allows the sequences to be human readable. The sequenced fragments may be subjected to sequencing quality control so to remove the nucleotides of low quality or remove a low-quality fragment altogether. This quality control is considered to be optional in some settings. These quality controlled sequenced fragments (auxiliary information present for each fragment like, cell barcodes or sequencing) may then be aligned to the genome/transcriptome or any selection of the portion of genome using genomic alignment tools. This specific step might be performed in alternative ways where, for example, a pseudoalignment strategy is used to identify the portion of the genome where a fragment originates from. Once, genomic location (either in terms on precise coordinates or in terms of genomic entity) of each fragment is determined, depending on the modality being accessed there might be intermediate steps such as peak calling in the case of single nuclei ATAC-Seq and single-cell CUT&TAG. The barcode information for each of the fragments or their derived genomic information (for example peaks) may be collated to create a cell-feature matrix. This cell-feature matrix represents the single-cell genomics data in a shareable form ready for actionable analysis. The actual storage format of this cell-feature form can be in either, HDF5, CSV, LOOM, ZARR or any other columnar data storage formats.

Identification of Assays

This step may be performed once the single-cell genomics dataset is stored in the memory. The method may, in a first step identify the different number of assays that exist in the dataset. With the advancement of single-cell genomics methods, it is now possible to sequence different genomics features from the same cells. One technique that can be used for this is Cellular Indexing of Transcriptomes and Epitopes by Sequencing (CITE-Seq), which allows quantification of both, gene expression (transcript abundance and diversity) as well as cell surface markers from the same cells. Therefore, one embodiment of the presently disclosed method of extracting a subsample of cells from a plurality of cells in a single-cell genomics dataset further comprises the step of identifying assays in the single-cell genomics dataset and sequences genomic features.

Filtering Out Cells

In one embodiment of the presently disclosed method of extracting a subsample of cells from a plurality of cells in a single-cell genomics dataset, cells are filtered out in a further step. This step may include filtering out cells having a number of features less than a predetermined lower limit and/or greater than a predetermined upper limit, or filtering out cells based on other characteristics.

In the example in which cells having a number of features less than a predetermined lower limit and/or greater than a predetermined upper limit are filtered out, or wherein threshold values are identified to classify cells as having too many or too few features, the method may create a normal distribution based on the same mean and sample variance and removes cells that have less than a certain percentage of being drawn from the distribution. Other suitable ways of performing feature filtering may be envisaged.

Normalization

The presently disclosed method may further comprise the step of normalizing the information about genomic features before generating the cell-cell neighborhood graph. The step of normalizing the information may be used to provide comparable quantified genomic features. The step may comprise defining the normalization that is applied. In order to speed up the process, the normalization may be applied when the single-cell genomics dataset is loaded to the memory. In the case of Single-Cell RNA sequencing (scRNA-Seq), a library size normalization method may be used. This normalization step divides the feature values of each cell by the total value from that cell and multiplies the resultant value by a constant scalar. This normalization step makes sure that there is a minimal effect of sequencing depth of individual cells on the downstream analysis. In the case of Single-Cell Assay for Transposase-Accessible Chromatin using sequencing (scATAC-Seq), the method may apply TF-IDF normalization (term-frequency, inverse document frequency). The TF value is calculated by dividing each cell by its sum of values and the IDF value is calculated by dividing the total number of cells by the vector consisting of number of cells where each gene is present. The scalar product of TF-IDF gives the normalized values. For cell surface markers, the method may perform CLR (centered-log ratio) normalization.

Feature Selection

The presently disclosed method may further comprise the step of performing feature selection by selecting a smaller subset of features from the information about genomic features before generating the cell-cell neighborhood graph. This step may rely on the assumption that only a small subset of genomic features can capture the diversity among the cells and that many features are redundant to each other. As a result of feature selection, a smaller subset of genomic features will be used for further analysis.

The choice of feature selection method may depend on the kind of single-cell genomics dataset being used. For scRNA-Seq datasets, feature selection may be performed based on the variance of genes. Because the variance and mean expression of genes are often correlated, the mean-variance trend may first be removed by dividing the genes into a desired number of bins based on their mean expression values. The genes with minimum variance in each bin are selected and a step-wise regression is performed between mean and variance to fit a curve through the selected genes from each of the bins. The resultant curve is used to regress out the residual variance from each of the gene, thus obtaining a corrected variance value. The genes with highest corrected variance are selected.

For scATAC-Seq datasets, the values may be normalized using TF-IDF and most prevalent peaks, i.e. ones with high average normalized values across cells are selected. The user can decide to choose top 'n' HVGs or prevalent peaks, where 'n' is any number of features.

Dimension Reduction

The method may further comprise the step of dimension reducing the single-cell genomics dataset before generating the cell-cell neighborhood graph. The dimension reduction may be performed using an incremental principal component analysis (PCA).

In one embodiment the normalized data is subject to dimension reduction. Dimension reduction techniques allow a reduction in feature space which helps amplify a signal to noise ratio. Dimension reduction may also serve the purpose of reducing data redundancy. PCA may be applied on e.g. single-cell RNA data. In the case of scATAC-Seq, the presently disclosed method may apply an incrementally updateable version latent semantic indexing technique. The choice of number of reduced dimensions to retain for further steps is configurable by a user. In the case of single-cell RNA-Seq, prior to subjecting data to PCA, the data may be scaled feature-wise to have zero mean and a unit standard deviation for each gene. The data may or may not be log-transformed before this step.

Generating the Cell-Cell Neighborhood Graph

The cell-cell neighborhood graph can be generated in various ways. In a preferred embodiment, the step of generating the cell-cell neighborhood graph from the single-cell genomics dataset comprises performing a k nearest neighbors (KNN) algorithm. In such an algorithm a graph is created, wherein the cells are represented as vertices. The vertices are connected via edges if at least one of the vertices is a k nearest neighbor of the other one. In order to decide how 'near' cells are to each other, it may be useful to compare quantified genomic features against each other, preferably wherein the quantified genomic features are normalized.

According to one example the k number of nearest neighbors of each cell is identified, where k is any positive integer provided by the user. The KNNs of each cell allow creation of a graph data structure of cells. In the graph, each vertex is a cell and the vertices are connected via edges. Two vertices are connected if at least one of them is a nearest neighbor of the other. The edge weight in the graph is inversely proportional to the distances between the cells. To calculate the distances between the cells, Euclidian distances or other suitable metrics may be used. Identification of KNNs for each cell by comparing each pair of cells is not scalable to a large number of cells. Hence, in one embodiment, an index of cells is created and then the nearest neighbors are queried over these cells. The distances between the KNN neighbors are converted into continuous form using a gaussian kernel. These values are treated as edge weights for the KNN graph. There are other possible alternatives to calculate graph structure of the data, for example one can create a shared nearest neighbor graph by calculating the common neighbors among every pair of cells that are KNN of each other. The presently disclosed method is agnostic to the approach of taken to create the cell-cell graph. In one embodiment an approximate version of KNN called HNSWlib is used to generate the cell-cell neighborhood graph from the single-cell genomics.

Figure 4:
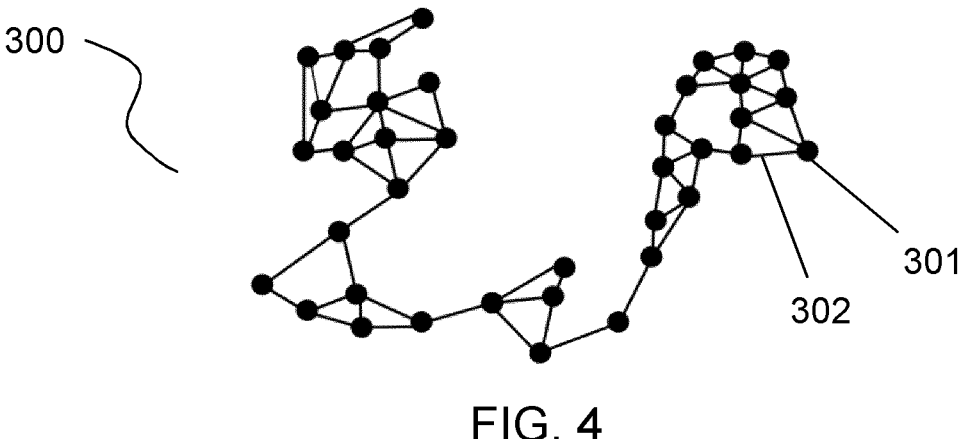
FIG. 4 shows an example of a cell-cell neighborhood graph according to the presently disclosed method of extracting a subsample of cells from a plurality of cells in a single-cell genomics.

FIG. 4 shows an example of a cell-cell neighborhood graph (300). In this example each vertex (301) of the graph is a cell (301). The vertices (301) are connected by edges (302). The edges (302) denote that the connected cells (302) are k-nearest neighbors.

Dividing Cells in the Cell-Cell Neighborhood Graph into Seed Cells and Non-Seed Cells The step of dividing cells in the cell-cell neighborhood graph into seed cells and non-seed cells can be implemented in several ways.

In a preferred embodiment the step comprises the steps of:
clustering the cells in the cell-cell neighborhood graph to obtain substantially even sized clusters of cells; and
choosing at least one cell from each cluster of cells and categorizing the chosen cells as seed cells, thereby dividing the cells into seed cells and non-seed cells.

The step of clustering the cells in the cell-cell neighborhood graph may be based on, for example, a Louvain, Leiden or Paris algorithm. This step may convert the cell-cell neighborhood graph to a dendrogram structure. The step of clustering the cells in the cell-cell neighborhood graph may comprise limiting the number of cells within each cluster to a minimum and a maximum number of cells. More specifically, the step of clustering the cells in the cell-cell neighborhood graph may comprise the step of converting the cell-cell neighborhood graph to a dendrogram structure, wherein each cell is represented as a leaf node and the leaves are connected to each other through branch point nodes in the dendrogram structure, wherein the step of clustering the cells in the cell-cell neighborhood graph comprises the step of partitioning the leaf nodes and branch point nodes into groups of cells, the groups having an upper bound and a lower bound. The upper bound is preferably set to a relatively small number, such that each group has only a small fraction of total number of cells, thus leading to a 'micro-clustering' wherein each group/partition of cells is highly homogenous. The upper bound may be a number that is smaller than, or equal to, 300, preferably smaller than, or equal to, 200, even more preferably smaller than, or equal to, 100. The lower bound may be, for example, 10. In one example, the lower bound is 10 and the upper bound is 200.

An example of a clustering process is described as follows: The cell-cell neighborhood graph of cells may be subject to clustering to obtain even sized clusters of cells. Multiple clustering strategies for graph data structure with community clustering methods exist. Preferably, a clustering method that has a runtime that scales linearly to the number of cells present in the graph is selected. This algorithm may convert the graph data structure into a dendrogram structure. In one embodiment the number of cells within each cluster can be limited within predetermined upper and lower bounds. The algorithm may be a greedy bottom up approach and hence the algorithm may start aggregating from the leaf nodes. In the dendrogram each cell represents a leaf node and these leaves are connected to each other through branch-point nodes. Each branchpoint node divides into two nodes which may both be a branchpoint or a leaf node or a combination of the two. The branchpoints nodes will eventually join upstream into a root node. First all the cells are ranked based on how many branchpoints nodes are between them and the root node. These ranks determine the order in which the cells will be taken up as candidates for cluster aggregation. The reasoning behind this is that the cells are prioritized for clustering based on how deep the dendrogram is at that location. The more branchpoints indicate that the cells have more subtle differences between them. The algorithm starts with the node with the highest rank and then moves to the parent branchpoint node of that cell, the other child node of that branchpoint node is automatically included into the cluster. Thereafter, the algorithm keeps moving to upstream branchpoints until including the upstream branchpoints will increase the size of the cluster to more than a predetermined threshold at which point the cluster is frozen and the algorithm moves to the next leaf node (cell) in the rank list that has not been included in any cluster. The other condition for halting the upstream traversal is when the sibling of a branchpoint has already been included into a cluster. Accordingly, in one embodiment of the presently disclosed method of extracting a subsample of cells from a plurality of cells in a single-cell genomics dataset each cell is represented as a leaf node and the leaves are connected to each other through branch point nodes in the dendrogram structure, wherein the step of clustering the cells in the cell-cell neighborhood graph comprises the step of ranking each cell based on how many branch point nodes that are between the cell and a root node of the dendrogram structure and clustering based on the ranking. Once all the leaf nodes are included into a cluster, the next step is to merge clusters together to make sure that each cluster has at least the number the cells configured by the user. Clusters are considered in the order in which they were created, and their size is less than the cutoff, they are merged with the cluster within the sibling branchpoint (i.e. the cluster they have the most recent common ancestor with). The merging is repeated until a minimum cluster size is obtained. If the sibling branchpoint has more than one cluster, then the cluster with minimum distance to the given cluster is considered for merging given the condition that the distance is not larger than a predetermined threshold. This clustering strategy with creation of dendrogram and bottom-up balanced clustering provides clusters of cells that have a remarkably high similarity amongst themselves and also are closely connected in the graph.

Alternatively, the step of clustering the cells in the cell-cell neighborhood graph may use a dynamic sampling approach. This approach may also depart from a dendrogram. Similar to the approach described above, it has the purpose of narrowing down the cells in each group to a pool of cells from which the seed cells can be randomly sampled. In one embodiment, the step of clustering the cells in the cell-cell neighborhood graph comprises the step of performing a first partitioning and for each partition of the first partitioning determining a number of sub-partitions based on a measure of strength of inter-connectivity of cells with each partition of the first partitioning. When a suitable number of sub-partitions has been determined, the actual step of performing sub-partitioning within the partitions of the first partitioning can be performed. In a further step the cells within each partition of the first partitioning may then be converted to a dendrogram structure indicating a hierarchical relationship between the cells.

Further Example of Division of Cells in the Cell-Cell Neighborhood Graph into Seed Cells and Non-Seed Cells According to one example, seed cells are identified by calculating two metrics for each individual cell (referred to as node in the neighbourhood graph): n-neighbourhood degree (NND) and neighbourhood-connectedness (NC). The degree of the node is calculated as the total number of other nodes this particular node is connected to. 1-neighbourhood degree is the sum of degree of all nodes that are connected to a given node. Hence, NND is computed by iterating neighbours of neighbours over n-step distance and captures the density of the connections around a given node in the graph. The second metric is neighbourhood connectedness that captures if a given number of connections are shared between many or few nodes. To calculate NC of each cell, the sum of shared nearest neighbour distances (Jaccard distance) between a node and all its neighbours is calculated. Thus, if a node is connected to other nodes that are strongly connected with each other, this node will get a high value for neighbourhood-connectedness.

For the next step, the algorithm uses partitioning of cells. Here, median NND and NC is calculated for each cluster of cells and the median value is used to adjust the sampling rate for each cluster. A higher median NND leads to reduction in sampling rate while a higher NC leads to a reduced sampling rate and vice-versa. Based on the sampling rate, the number of cells to be sampled from each of the clusters are determined. Each cluster is then sub-clustered, wherein the number of sub-clusters are the same as the number of cells to be sampled; one cell is then sampled from each of the sub-clusters.

These sampled cells are referred to as 'seed' cells.

Figure 7A:
FIG. 7 shows visualization of dendrogram comprising clusters of cells.

FIG. 7 shows visualization of dendrogram comprising clusters (401) of cells. FIG. 7A shows clusters obtained by applying a straight cut algorithm. In this example it can be seen that the clusters (401) have variation in size (i.e. the number of cells within a cluster). Each circle (401) represents a cluster of cells. The size of the circle denotes the number of cells in the cluster. The dendrogram has a root node (403). The dendrogram has a number of branchpoints (404). The branchpoints and the structure of the branchpoints and clusters can be said to provide information about how similar the clusters (401) are. The more similar the clusters are, the closer their shared branchpoint is.

Figure 7B:
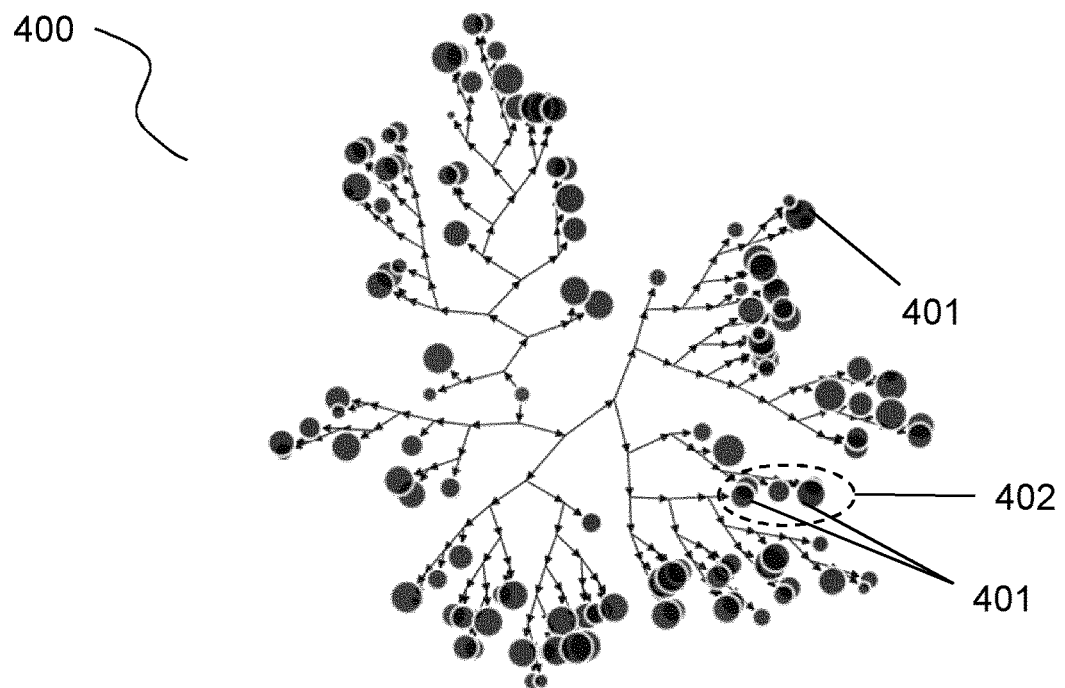

FIG. 7B shows clusters obtained by applying a balanced cut algorithm. This algorithm yields clusters of more similar sizes than the straight cut algorithm. The figure also illustrates how large clusters (402) can be broken down into smaller clusters (401) in the balanced cut algorithm.

Figure 8A:
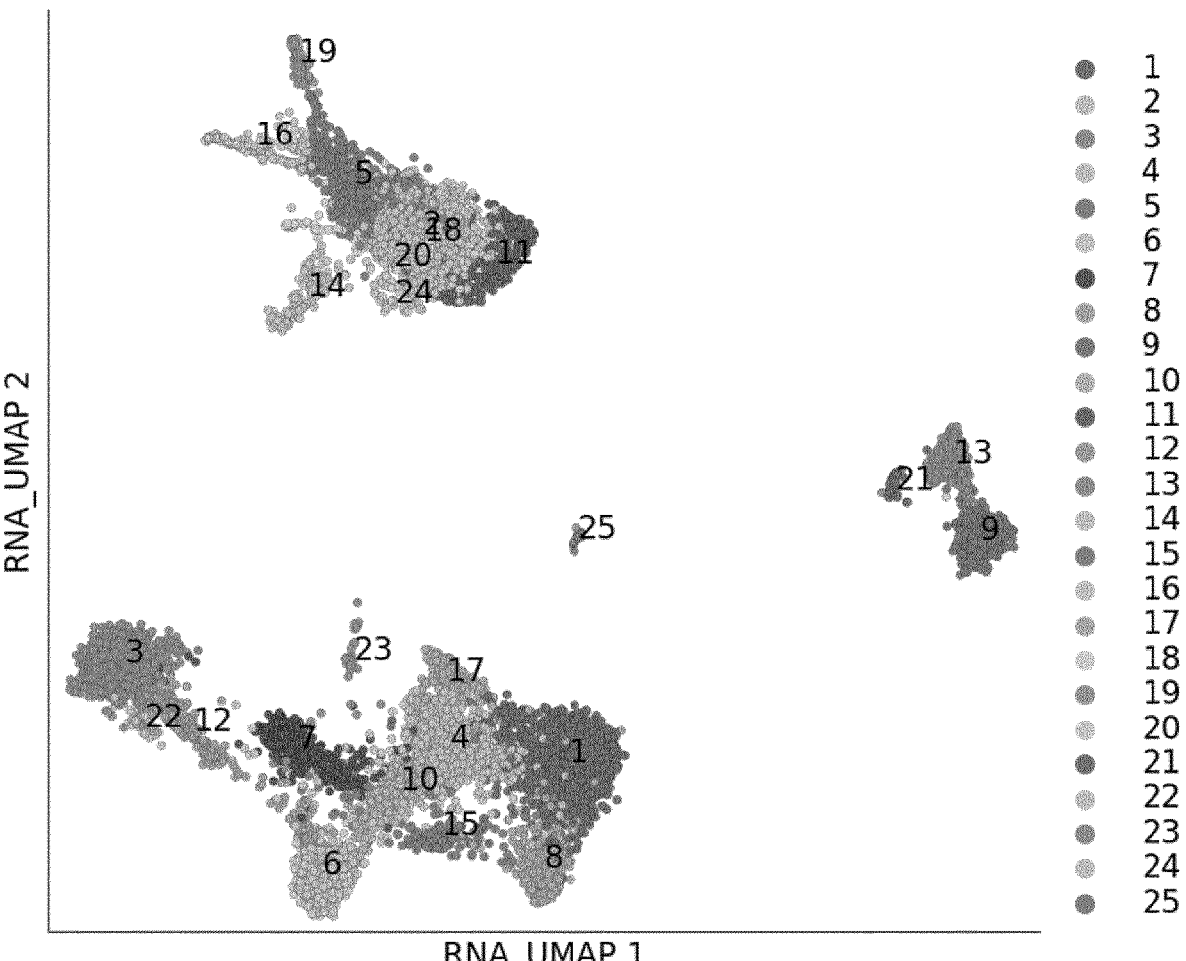
FIG. 8 shows an example of clustering.
Figure 8B:
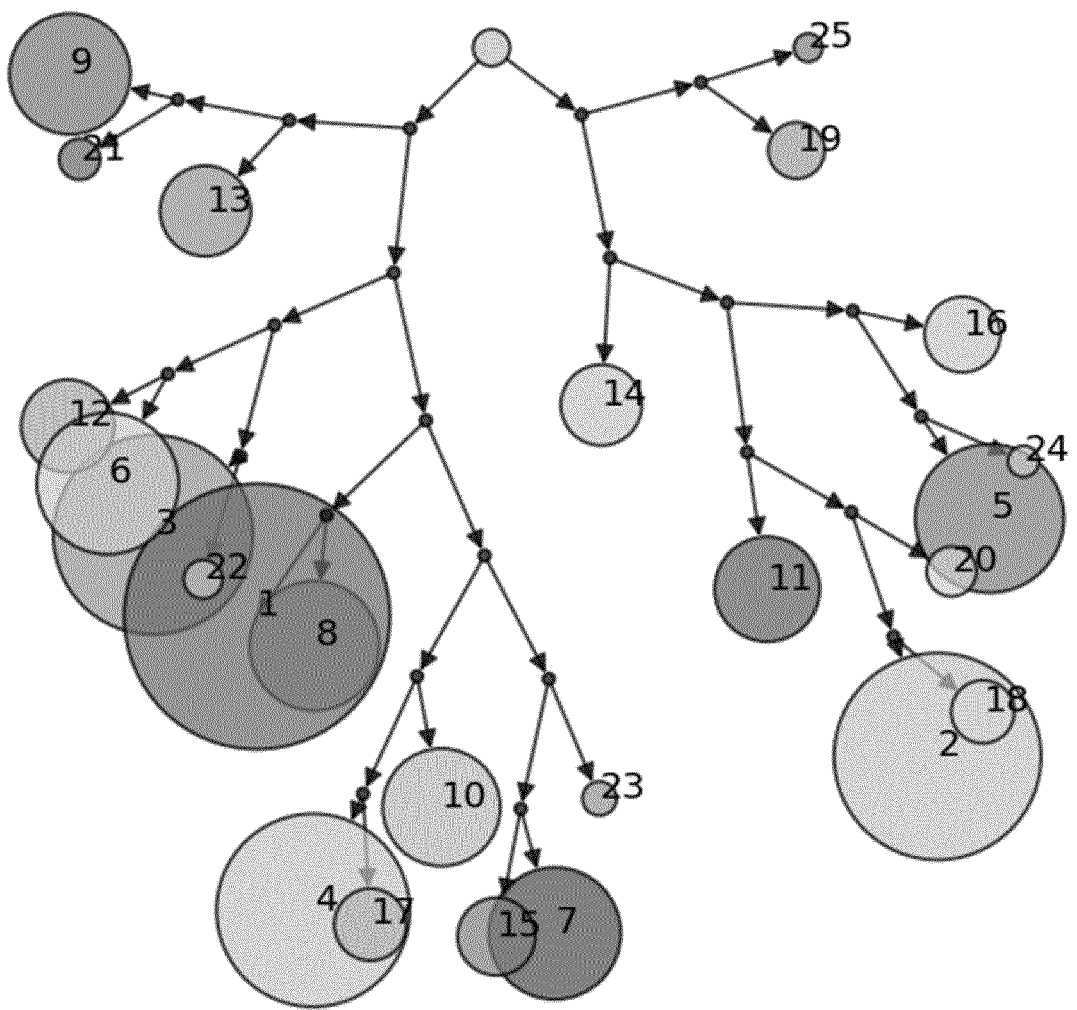

FIG. 8 shows a further example of clustering. FIG. 8A shows an example of how cells have been divided into clusters (numbered 1-15). The cells are numbered based on their cluster identity. By applying an algorithm, in this case a Paris algorithm, a dendrogram of cells is created, which is shown in FIG. 8B. Cells that form a cluster are merged into a single node (numbered circles in FIG. 8B). The sizes of circles indicate the number of cells in the clusters. The unlabeled node at top of dendrogram is the root of dendrogram.

When the clusters have been created, the presently disclosed method may, in a further step, choose at least one cell from each cluster of cells and categorize the chosen cells as seed cells. The cells that are not chosen are categorized as non-seed cells.

Preferably, a minimum of one cell must be chosen from each cluster. Cells can be chosen randomly or based on some measure, for example, how central they are in the cluster. The seed cells capture the heterogeneity of the cells. Capturing graph topology may be important for ensuring that differentiation trajectories and heterogeneity within rare populations is captured.

Setting Prizes

The presently disclosed method of extracting a subsample of cells from a plurality of cells in a single-cell genomics dataset preferably comprises traversing the cell-cell neighborhood graph using a PCST algorithm to obtain a subsample of cells. Before the PCST algorithm is performed, prized must be assigned to the seed cells and non-seed cells in the cell-cell neighborhood graph. One way of setting the prizes is to assign a single first prize to all seed cells and a single second prize to all non-seed cells. The single first prize will typically be higher than the single second prize. The single first prize may be an arbitrarily high prize. The value may be guided by the number of cells in the graph. The required value grows with the number of cells present in the graph. Having an extremely high value will typically not have an adverse effect on the algorithm. The only objective for setting the prize is to ensure that the cell will be considered for traversal in the later steps. The non-seed cells may be given a value of 0, which means that the traversal algorithm will have no incentive for including those cells.

In an alternative embodiment the prizes are instead individually configurable for the individual seed-cells and non-seed cells. For example, prizes on the seed cells can be set to be proportional to their in-degree, i.e. number of other cells that a given cell is connected with in the graph. Also, based on the concept of neighborhood degree of the cells (i.e. cumulative degree of the cells that are adjacent to a given cell in the graph), one might assign greater than 0 values to non-seed cells in a sparse region of the graph to encourage smoother coverage of the manifold.

One might choose to set no or very low penalty on edges of the graph, this ensures that even those seed cells that are located further away from other seed cells can be easily captured during graph traversal. In our prototype we use 1—edge weight in the KNN graph as the penalty on edges. Since, the edge weights are bounded within 0 and 1 values, the penalties are also within those bounds. Alternatively, one might choose to set edge penalties based on neighborhood densities such that traversal is encouraged or discouraged in different parts of the graph.

Figure 5:
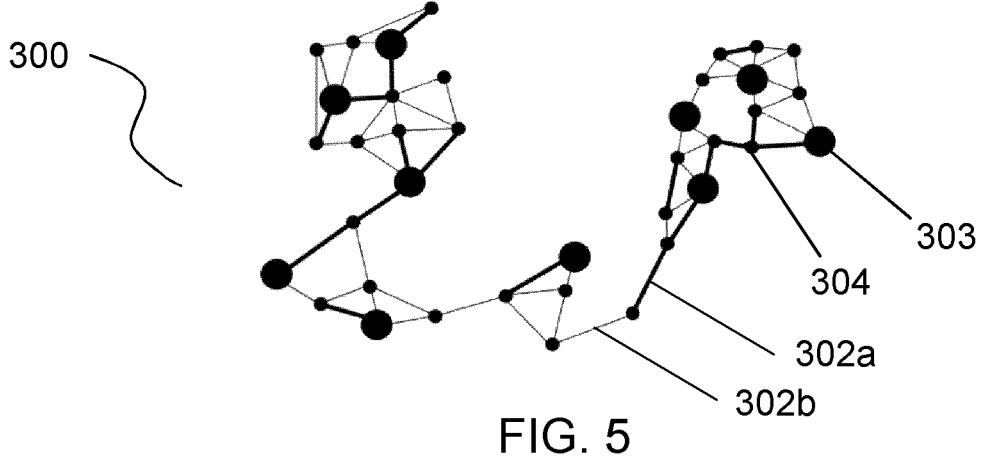
FIG. 5 shows an example of a cell-cell neighborhood graph, wherein the cells have been divided into seed cells and non-seed cells.

FIG. 5 shows an example of a cell-cell neighborhood graph (300). In this example the cells have been divided into seed cells (303) and non-seed cells (304). Preferably, each seed cell (303) (larger dots in the figure) is assigned a first prize selected from a first score set. Preferably, each non-seed cell (304) (smaller dots in the figure) is assigned a second prize selected from a second score set. The edges (302) between the cells (303, 304) are assigned penalties selected from a third score set. In the example, the widths of the edges visualize these penalties. As an example, the edge 302$a$ is thicker than edge 302$b$, which indicates that edge 302$a$ has a higher penalty than edge 302$b$.

Further Example of Setting Prizes

There are different approaches for assigning prizes. According to one example all the seed cells are assigned a constant prize value. For example, an initialization value of 10 may be used. The edge penalty E$_p$ for each edge may then be calculated as following:

$$E_p = E_{cm} \cdot E_{bw}^{-E_w}$$

wherein, E$_{cm}$ and E$_{bw}$ are user provided parameters, edge cost multiplier and edge bandwidth, respectively and E$_w$ is the edge weight in the graph. Higher values for E$_{cm}$ will make reaching remote cells in the graph more difficult but at the same time will discourage inclusion of non-seed cells in the downsampled set. Higher E$_{bw}$ accentuates the difference among edge penalties. In one example, E$_{cm}$=1 and E$_{bw}$=10

Once, the prizes on the seed cells and penalties on all the edges are set, POST algorithm may be performed, which is further described and exemplified below.

Traversing the Cell-Cell Neighborhood Graph Using a Prize Collecting Steiner Tree Algorithm Once the prizes are set, the method then uses an implementation of prize collecting steiner trees (POST). The cell-cell neighborhood graph along with set prizes is provided to this POST algorithm. In one embodiment the algorithm is configured to include as many seed cells as possible and as few non-seed cells as possible. In one embodiment the POST starts traversing through the cell-cell neighborhood graph with objective of including all the seed nodes with minimum possible non-seed node included. It is possible that the cell-cell graph is already disconnected at this point. It is a plausible scenario when very discrete populations are present in the dataset. In such cases, the POST algorithm may be executed on each of the disconnected components of the graph separately. Hence, in one embodiment of the presently disclosed method, the cell-cell neighborhood graph comprises disconnected subgraphs, wherein the POST algorithm is performed on all subgraphs. As the results of POST graph traversal, the subsample of cells is obtained. These may comprise non-seed nodes to ensure that the subsample of cells from the cell-cell neighborhood graph (or the subgraph in the case where the graph was disconnected) are connected. As stated above the cells may be represented as vertices and connected by edges, wherein each edge represents a magnitude of similarity between the cells. In one embodiment penalties are assigned to the edges between the vertices, wherein the penalties represent a degree of dissimilarity between the cells of the vertices. The penalties can be taken into account when traversing the cell-cell neighborhood graph. In one embodiment of the present method iterative subsampling is performed by creating a new cell-cell graph using subsampled cells and applying clustering and seed identification steps, followed by a new POST search. User may decide to perform as many iterations of subsampling as required to obtain a necessary down sampling size.

Figure 6:
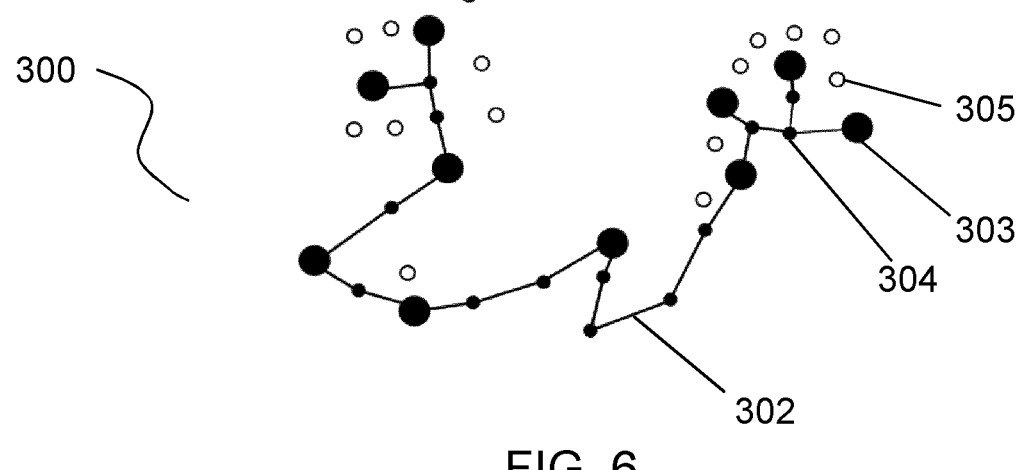
FIG. 6 shows an example of a cell-cell neighborhood graph, wherein a subsample of cells have been extracted from the plurality of cells in the single-cell genomics dataset.

FIG. 6 shows an example of a cell-cell neighborhood graph (300) according to the presently disclosed method of extracting a subsample of cells from a plurality of cells in a single-cell genomics dataset, wherein a subsample of cells (303, 304) have been extracted from the plurality of cells (i.e. all cells in the graph (300)) in the single-cell genomics dataset. In this visualization the filled dots (303, 304) represent the seed and non-seed cells that are included in the subsample of cells. The empty dots (305) represent dots that were not included in the subsample of cells. The edges (302) that are visible in the figure are the edges traversed by POST to ensure that all cells in the graph are connected.

Figure 9A:
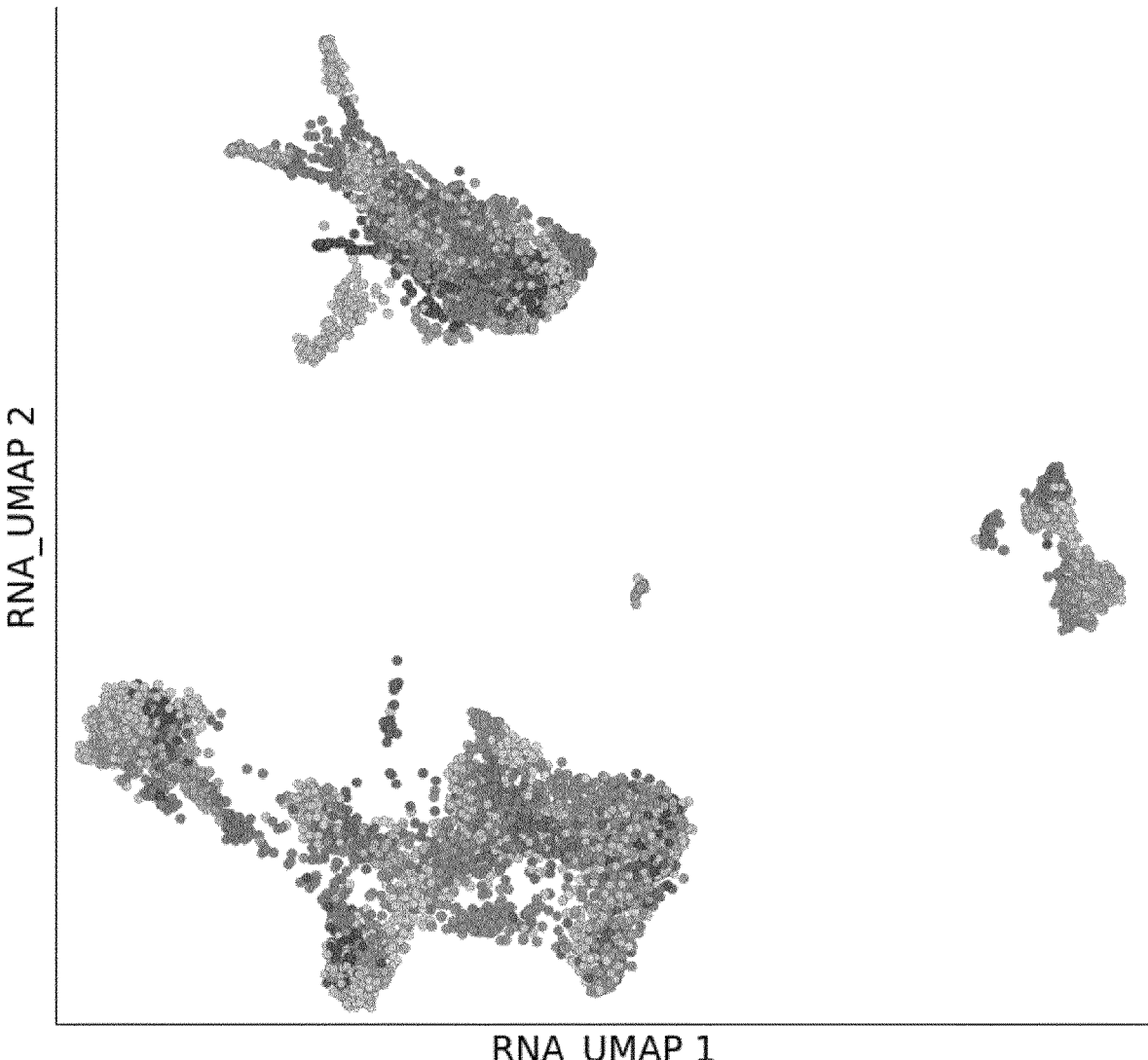
FIG. 9 shows a further example of clustering and the resulting subsample of cells after traversing the cell-cell neighborhood graph using a prize collecting steiner tree algorithm (POST).
Figure 9B:
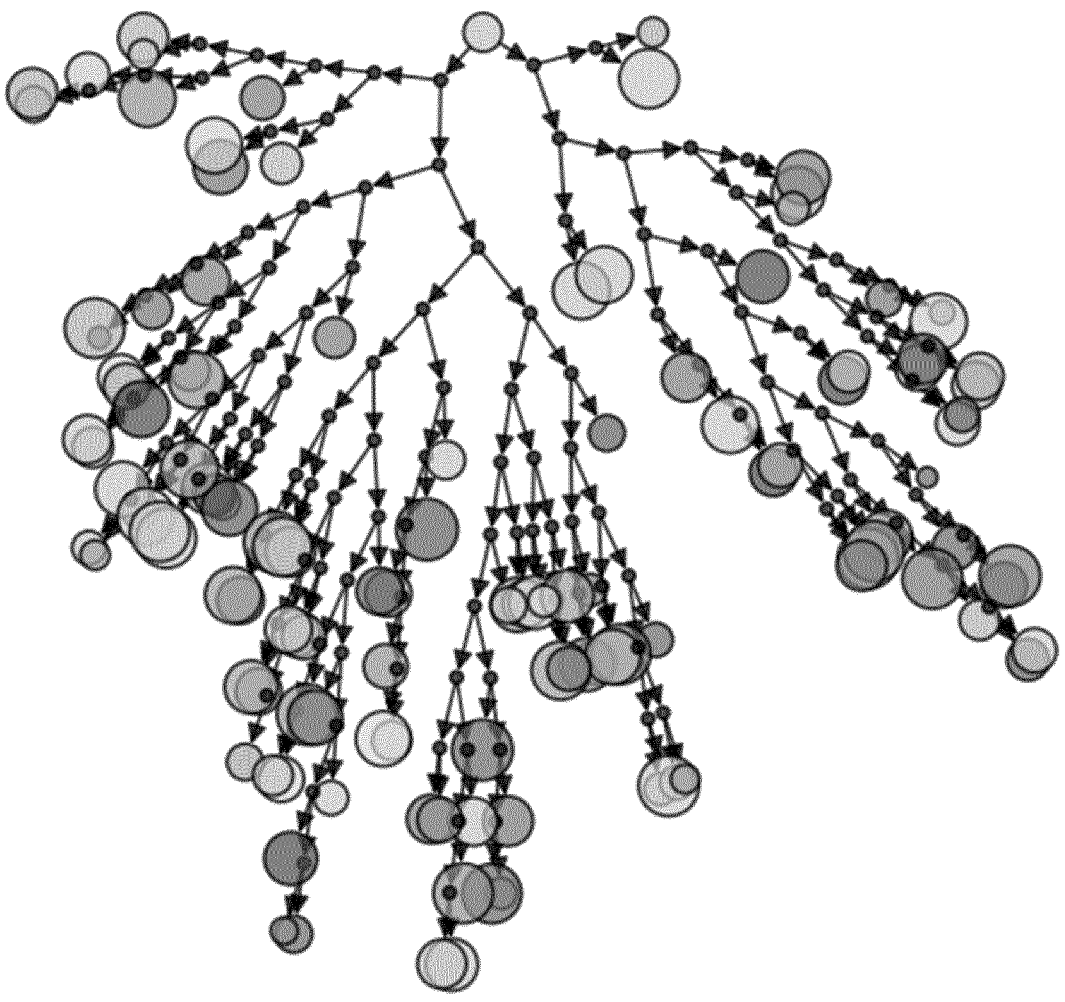
Figure 9C:
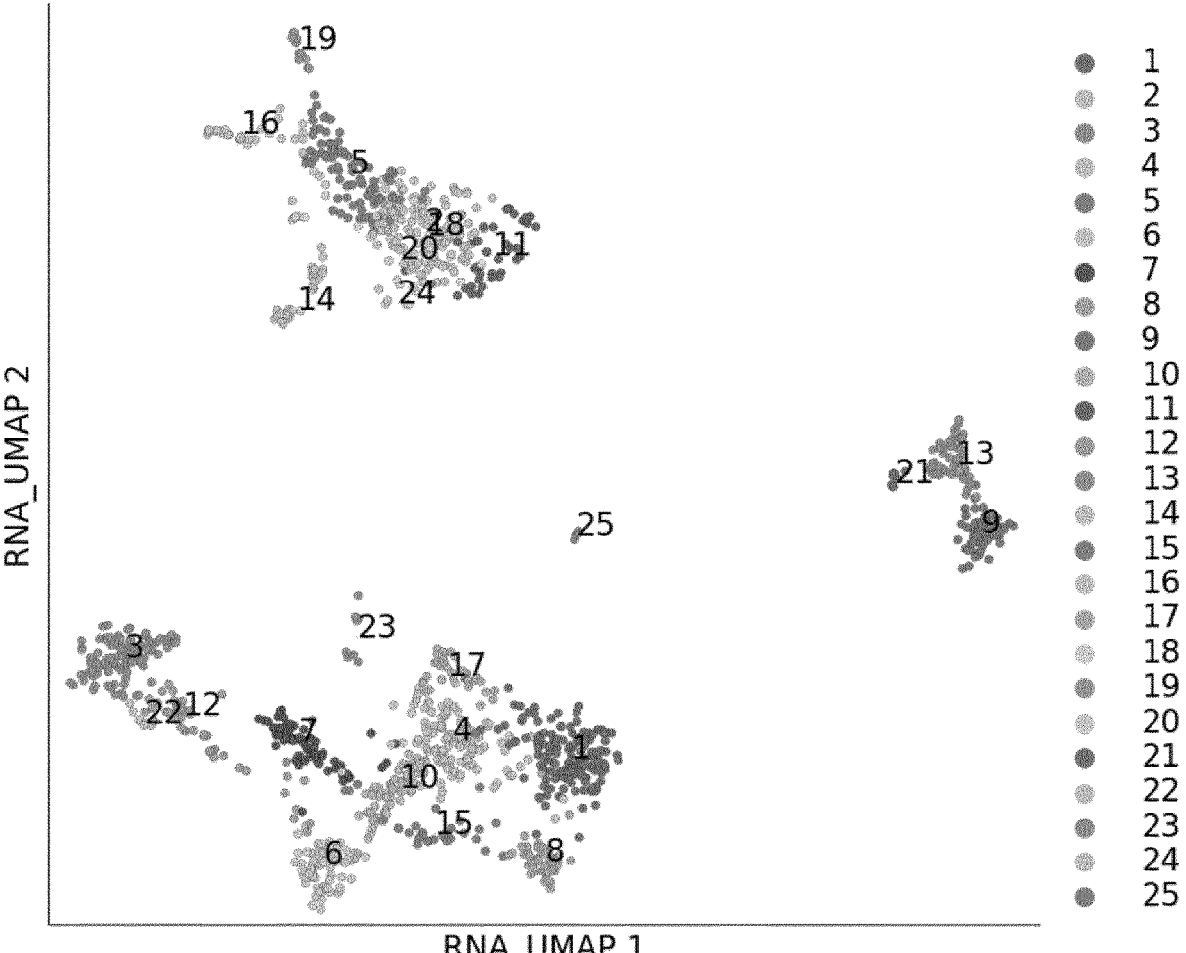

FIG. 9 shows a further example of clustering and the resulting subsample of cells after traversing the cell-cell neighborhood graph using a POST algorithm. FIG. 9A shows the result of clustering using a balanced cut approach. The clusters and their sizes are then visualized on a coalesced dendrogram in FIG. 9B. FIG. 9C shows the subsampled cells as a result of running POST on the cell-cell neighborhood graph of cells with the prizes set. All the clusters are represented in the subsample, even the clusters with smaller number of cells.

Computer System

Figure 3:
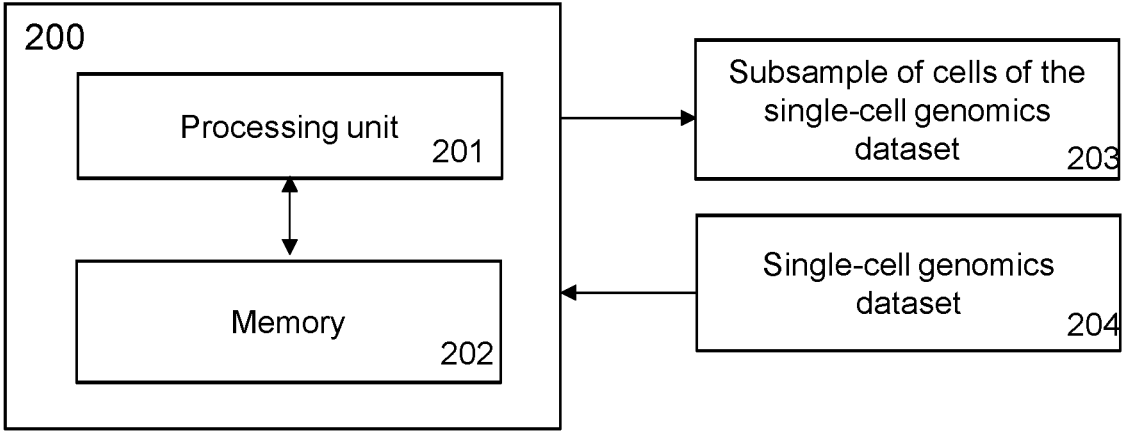
FIG. 3. shows a schematic view of one embodiment of the presently disclosed system for extracting a subsample of cells from a plurality of cells in a single-cell genomics dataset.

The present disclosure further relates to a computer system for extracting a subsample of cells from a plurality of cells in a single-cell genomics dataset. The system comprises a processing unit, which may comprise any suitable single- or multi-processor central processing unit. The processing unit may operate using any suitable instruction set architecture, such as an instruction set architecture based on CISC and RISC, including, but not limited to, x86, ARMv6-v8, x86-64, PowerPC. The system further comprises a memory, which may have any suitable memory structure. Typically the memory structure will comprise one or several random-access memories (RAM) in the form of a static random-access memory (SRAM) and/or a dynamic random-access memory (DRAM). The processing unit is configured to carry out any variant of the presently disclosed method of extracting a subsample of cells from a plurality of cells in a single-cell genomics dataset. A schematic view of one embodiment of the presently disclosed computer system (200) is shown in FIG. 3. The computer system (200) comprises a processing unit (201) and a memory (202). A single-cell genomics dataset (204) is loaded into the memory (202). After having performed the method of extracting a subsample of cells from a plurality of cells in a single-cell genomics dataset, a subsample of cells (203) of the cells of the single-cell genomics dataset is delivered by the computer system in any suitable format. In a preferred embodiment the processing unit is configured to perform the steps of:

loading a single-cell genomics dataset represented in at least two dimensions into the memory, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph;

dividing the cells in the cell-cell neighborhood graph into seed cells and non-seed cells;

assigning at least one first prize to the seed cells and at least one second prize to the non-seed cells in the cell-cell neighborhood graph; and traversing the cell-cell neighborhood graph using a prize collecting steiner tree algorithm to obtain a subsample of cells.

Further Example and Result of for an Implementation of the Method

Figure 10A:
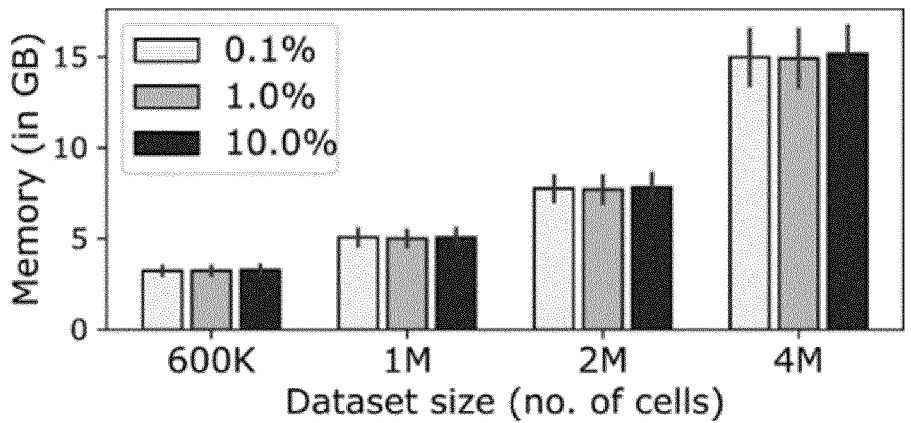
FIG. 10A-B show examples of use of memory (RAM) for the subsampling method for a number of data sizes, and the time consumption for executing the subsampling method.
Figure 10B:
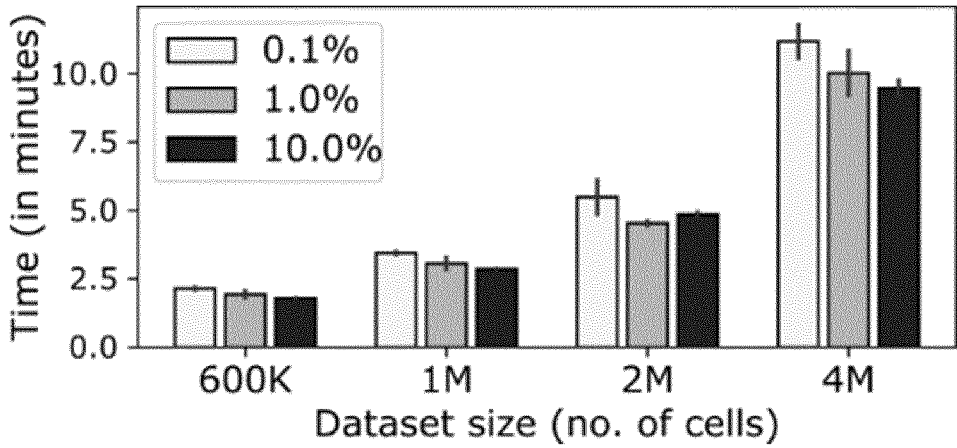
Figure 11:
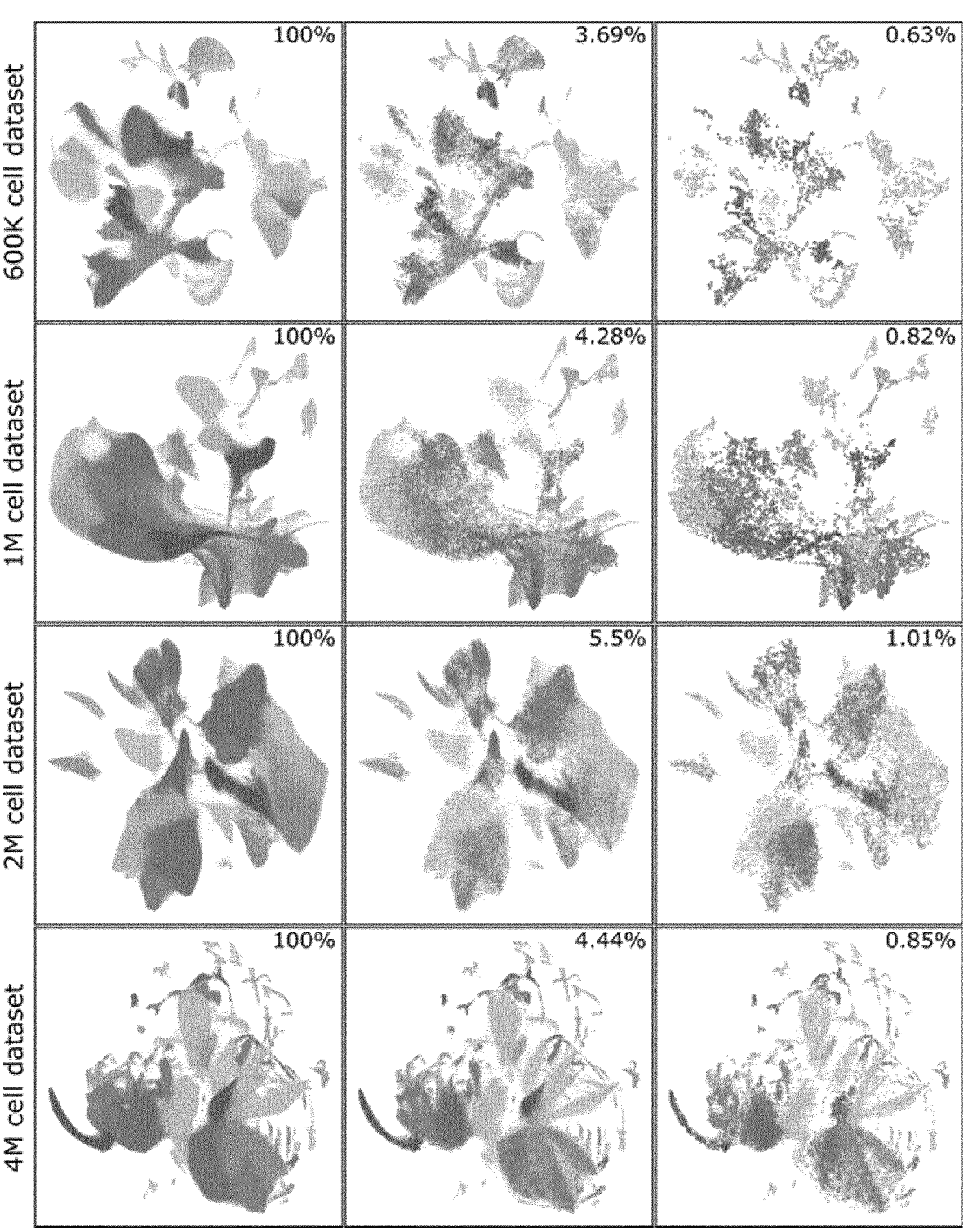
FIG. 11 show visualizations of a number of examples of subsampling

According to one example of an implementation, the method identifies landmark points in the graph (seed cells), and then tries to find paths to connect those seed cells using a POST algorithm (FIGS. 4-6). An implementation of POST with near-linear time complexity is used to achieve fast and scalable downsampling on millions of cells. It was found that an implementation was able to perform downsampling on datasets with up to 4 million cells using less than 20 GB of RAM (FIG. 10A). In addition, downsampling took less than 3 minutes on the 1 million cell dataset and less than 15 minutes in the case of 4 million cell dataset (FIG. 10B). UMAP visualization of four atlas scale datasets indicates that even with downsampling to ~1% of cells, cells belonging to all clusters across the UMAP space were sampled (FIG. 11).

Furthermore, for a quantitative analysis of downsampling the degree of connections subsampled cells make with other subsampled cells in the original neighbourhood graph was analyzed. A high frequency of zero-degree values indicates that many cells are disconnected from other subsampled cells and is a marker of poor subsampling, indicating that intermediary cell states are missing in the subsampled set. When comparing the number of disconnected cells between the present method (referred to as Scarf) with randomly subsampled cells from four atlas-scale datasets, 100% of Scarf-subsampled cells displayed non-zero degree values across all datasets, while random sampling resulted in non-zero degree values in 18.9%-26.9% of cells. (FIG. 12).

Two of the primary objectives of downsampling are to decrease redundancy in the dataset and preserve rare cell types/states. These two objectives can be accessed by calculating the change in proportion of cells from each cluster after downsampling. In the example, the implementation was able to reduce the proportion of cells from larger clusters while simultaneously increasing the proportion of cells from smaller clusters (FIG. 13). The proportion of cells from the smallest cluster in each of the datasets increased between 8.13 and 16.82 folds while the proportion of cells from the largest cluster decreased between 3.35 and 5.26 folds. In comparison, random clustering did not show any increase in proportion of smaller clusters beyond 1.5 fold or decrease in proportion of larger clusters beyond 1.01 fold. As a result, random clustering has a low probability to sample rare clusters. For example, the smallest cluster in the atlas-scale datasets had none of the cells sampled in 20% (1M cells dataset), 40% (2M cells dataset) and 20% (4M cells dataset) (n=10) of random samplings. In contrast, all clusters were sampled using Scarf, regardless of original cluster size.

Figure 14:
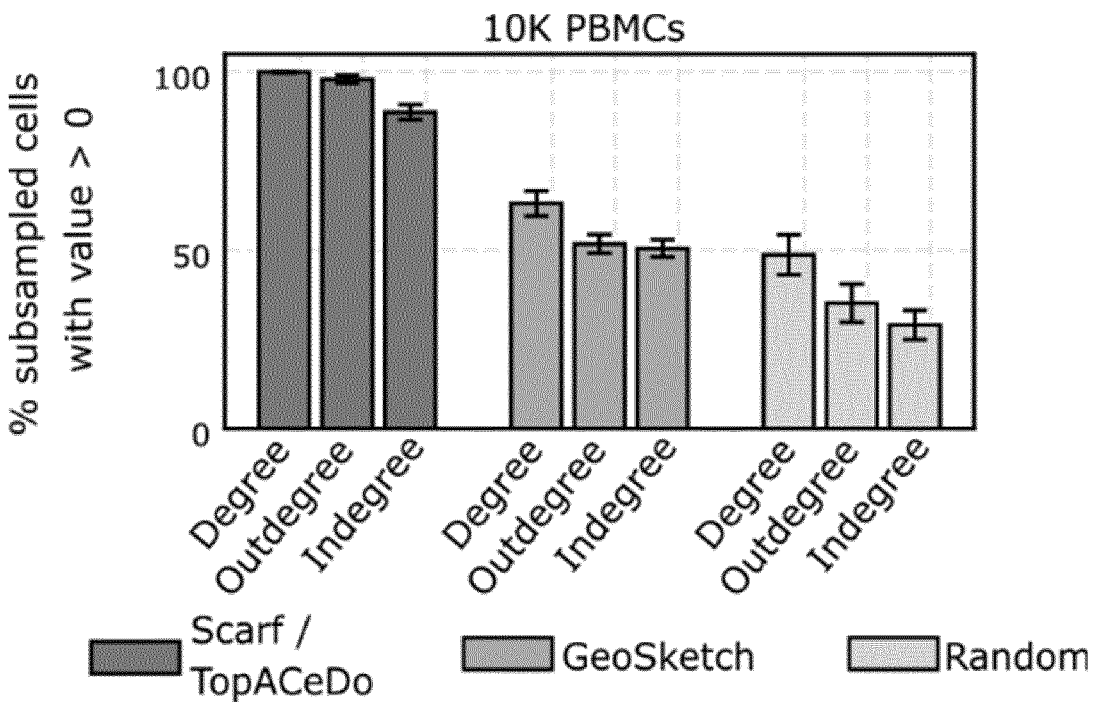
FIG. 14 show a comparison between the implementation, random sampling and another sampling tool in terms of degrees of connections subsampled cells make with other subsampled cells in the original neighbourhood (non-zero degrees shown).
Figure 15:
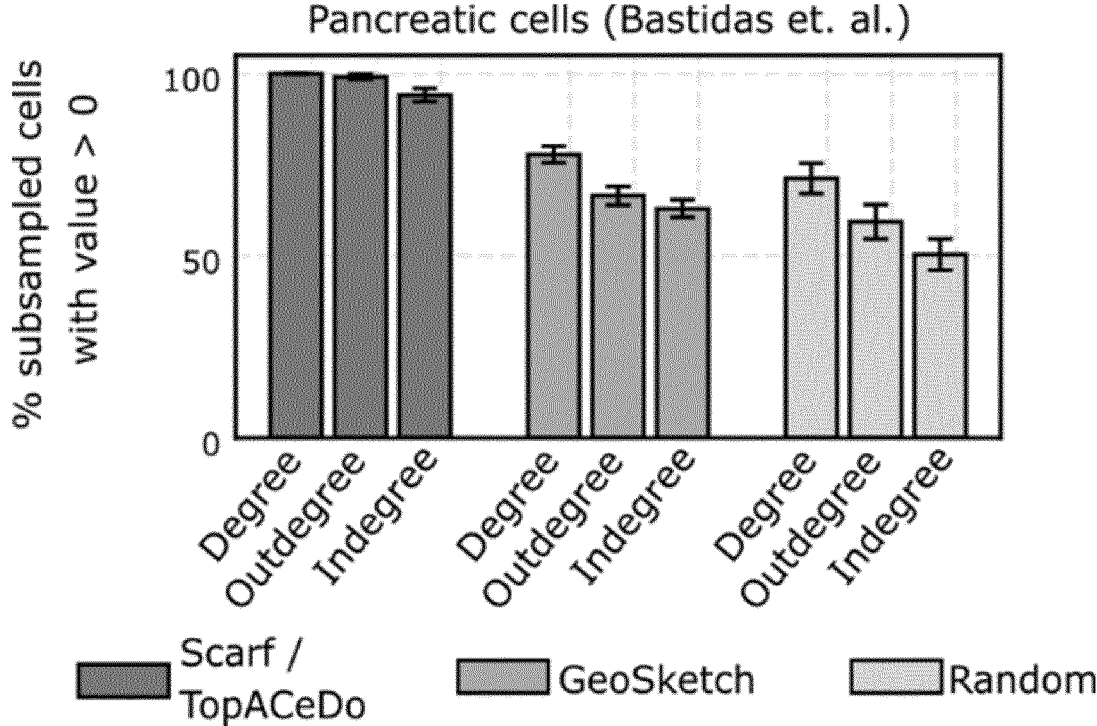
FIG. 15 show another comparison between the implementation, random sampling and another sampling tool in terms of degrees of connections subsampled cells make with other subsampled cells in the original neighbourhood (non-zero degrees shown).

Further comparison between the implementation against random sampling and another sampling tool, GeoSketch, is presented in FIGS. 14 and 15. Two contrasting small scale datasets consisting of either 10K PBMC cells of distinct cell types (provided by 10X Genomics) or 3.5K pancreatic cells within a continuum of differentiation were used. Visualization of progressively increasing level of downsampling on each of these datasets, showed that the present method was able to capture the cells throughout the UMAP. Running 100 iterations of downsampling with either the present method, GeoSketch or random sampling, 100% of downsampled cells selected by Scarf had a non-zero degree on both the datasets, while the same measurement for GeoSketch was 66.9% and 75.9%, and for random sampling 49.5% and 70.3% in the PBMC and pancreatic cell datasets, respectively (FIGS. 14 and 15).

Further Details of the Invention

1. A computer-implemented method of extracting a subsample of cells from a plurality of cells in a single-cell genomics dataset, the method comprising the steps of:

obtaining a single-cell genomics dataset represented in at least two dimensions, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph;

dividing the cells in the cell-cell neighborhood graph into seed cells and non-seed cells;

assigning at least one first prize to the seed cells and at least one second prize to the non-seed cells in the cell-cell neighborhood graph; and traversing the cell-cell neighborhood graph using a prize collecting steiner tree algorithm to obtain a subsample of cells.

2. The method according to item 1, further comprising the step of dimension reducing the single-cell genomics dataset before generating the cell-cell neighborhood graph.

3. The method according to item 2, wherein the step of dimension reducing the single-cell genomics dataset comprises an incremental principal component analysis.

4. The method according to any one of the preceding items, wherein the such as a cell barcode, for each cell.

5. The method according to any one of the preceding items, wherein the information about genomic features in the second dimension comprises quantified genomic features, such as an annotated gene, and/or a genomic location in coordinate form of a genomic assembly, and/or a number of cut sites in an identified accessible region, and/or a number of cDNA fragments for each gene, and/or a DNA/RNA oligonucleotide, a degree of methylation or any other epigenetic mark on a genomic loci.

6. The method according to any one of the preceding items, wherein the single-cell genomics dataset is a single-cell RNA-Seq dataset, a single-cell ATAC-Seq dataset, CITEseq dataset, or similar.

7. The method according to any one of the preceding items, wherein the single-cell genomics dataset is represented as a two-dimensional matrix.

8. The method according to any one of the preceding items, wherein the step of generating the cell-cell neighborhood graph from the single-cell genomics dataset comprises performing a k nearest neighbors algorithm.

9. The method according to item 8, wherein the k nearest neighbors algorithm comprises identifying k nearest neighbors of each cell, wherein k is a positive integer, and creating a cell-cell neighborhood graph wherein the cells are represented as vertices and the vertices are connected via edges if at least one of the vertices is a k nearest neighbor of the other one.

10. The method according to any one of the preceding items, wherein the step of dividing the cells in the cell-cell neighborhood graph into seed cells and non-seed cells comprises the steps of:
    clustering the cells in the cell-cell neighborhood graph to obtain substantially even sized clusters of cells;
    choosing at least one cell from each cluster of cells and categorizing the chosen cells as seed cells, thereby dividing the cells into seed cells and non-seed cells.

11. The method according to item 10, wherein the step of clustering the cells in the cell-cell neighborhood graph comprises a Louvain, Leiden or Paris algorithm.

12. The method according to item 10, wherein the step of clustering the cells in the cell-cell neighborhood graph converts the cell-cell neighborhood graph to a dendrogram structure.

13. The method according to item 10, wherein the step of clustering the cells in the cell-cell neighborhood graph comprises limiting the number of cells within each cluster to a minimum and a maximum number of cells.

14. The method according to item 12, wherein each cell is represented as a leaf node and the leaves are connected to each other through branch point nodes in the dendrogram structure, wherein the step of clustering the cells in the cell-cell neighborhood graph comprises the step of ranking each cell based on how many branch point nodes that are between the cell and a root node of the dendrogram structure and clustering based on the ranking.

15. The method according to any one of the preceding items, wherein a single first prize is higher than a single second prize, preferably wherein the second prize is 0.

16. The method according to any one of items 1-14, wherein the at least one first prize and the at least one second prize are individually configurable prizes for the individual seed-cells and non-seed cells.

17. The method according to any one of the preceding items, wherein the cells represented as vertices are connected by edges, wherein each edge represents a magnitude of similarity between the cells.

18. The method according to any one of the preceding items, further comprising the step of assigning penalties to edges between the vertices, wherein the penalties represent a degree of dissimilarity between the cells of the vertices.

19. The method according to any one of the preceding items, wherein the step of traversing the cell-cell neighborhood graph using a prize collecting steiner tree algorithm comprises the step of including as many seed cells as possible and as few non-seed cells as possible.

20. The method according to item 19, wherein the sub-sample of cells are connected.

21. The method according to any one of the preceding items, wherein the cell-cell neighborhood graph comprises disconnected subgraphs, wherein the prize collecting steiner tree algorithm is performed on all subgraphs.

22. The method according to any one of the preceding items, further comprising the step of loading the single-cell genomics dataset into a computer memory in partitions fitting the memory before the other steps are performed.

23. The method according to any one of the preceding items, further comprising the step of identifying assays in the single-cell genomics dataset and sequences genomic features.

24. The method according to any one of the preceding items, further comprising the step of filtering out cells, such as filtering out cells having a number of features less than a predetermined lower limit and/or greater than a predetermined upper limit, before generating the cell-cell neighborhood graph.

25. The method according to any one of the preceding items, further comprising the step of normalizing the information about genomic features before generating the cell-cell neighborhood graph.

26. The method according to any one of the preceding items, further comprising the step of performing feature selection by selecting a smaller subset of features from the information about genomic features before generating the cell-cell neighborhood graph.

27. A computer program having instructions which, when executed by a computing device or computing system, cause the computing device or computing system to carry out the method of extracting a subsample of cells from a plurality of cells in a single-cell genomics dataset according to any one of items 1-26.

28. A computer system comprising:
    a memory; and
    a processing unit configured to perform the steps of:
        loading a single-cell genomics dataset represented in at least two dimensions into the memory, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph;

dividing the cells in the cell-cell neighborhood graph into seed cells and non-seed cells;

assigning at least one first prize to the seed cells and at least one second prize to the non-seed cells in the cell-cell neighborhood graph; and traversing the cell-cell neighborhood graph using a prize collecting steiner tree algorithm to obtain a subsample of cells.

29. A computer-implemented method of extracting a subsample of cells from a plurality of cells in a single-cell genomics dataset, the method comprising the steps of:

obtaining a single-cell genomics dataset represented in at least two dimensions, wherein information about each cell is represented in a first dimension and information about genomic features of the cells is represented in a second dimension;

determining similarities of the genomic features of the cells and generating a cell-cell neighborhood graph from the single-cell genomics dataset, wherein the cells are represented as vertices in the cell-cell neighborhood graph and the distances between the vertices correspond to said similarities;

defining some cells in the cell-cell neighborhood graph as seed cells and defining remaining cells as non-seed cells;

assigning at least one first prize to the seed cells and at least one second prize to the non-seed cells in the cell-cell neighborhood graph, wherein the first prize is higher than the second prize; and extracting the subsample of cells by exposing the cell-cell neighborhood graph to a prize collecting steiner tree algorithm.

REFERENCE

Publication 'Scarf: A toolkit for memory efficient analysis of large-scale single-cell genomics data', May 3, 2021, Parashar Dhapola, Johan Rodhe, Rasmus Olofzon, Thomas Bonald, Eva Erlandsson, Shamit Soneji, Göran Karlsson, doi: https://doi.org/10.1101/2021.05.02.441899, https://www.biorxiv.org/content/10.1101/2021.05.02.441899v1.full, is hereby incorporated by reference in its entirety.

The invention claimed is:

1. A computer-implemented method of down-sampling a single-cell genomics dataset having an original manifold by extraction of a subsample of cells from a plurality of cells in a single-cell genomics dataset, the method comprising the steps of:

obtaining a single-cell genomics dataset represented in at least two dimensions, wherein information about each cell is represented in a first dimension and information about genomic features is represented in a second dimension;

generating a cell-cell neighborhood graph from the single-cell genomics dataset, the cell-cell neighborhood graph providing information about similarities of the genomic features of the cells, wherein the cells are represented as vertices in the cell-cell neighborhood graph, wherein the step of generating the cell-cell neighborhood graph from the single-cell genomics dataset comprises performing a k nearest neighbors algorithm, wherein the k nearest neighbors algorithm comprises identifying k nearest neighbors of each cell, wherein k is a positive integer, and creating a cell-cell neighborhood graph wherein the cells are represented as vertices and the vertices are connected via edges if at least one of the vertices is a k nearest neighbor of the other one;

dividing the cells in the cell-cell neighborhood graph into computational seed cells and non-seed cells, wherein the seed cells are selected to capture a heterogeneity of the cells;

assigning at least one first prize to the seed cells and at least one second prize to the non-seed cells in the cell-cell neighborhood graph; and traversing the cell-cell neighborhood graph using a prize collecting steiner tree algorithm, wherein the algorithm is configured to include as many seed cells as possible and as few non-seed cells as possible, to obtain a subsample of cells preserving the original manifold.

2. The method according to claim 1, wherein the step of clustering the cells in the cell-cell neighborhood graph comprises limiting the number of cells within each cluster to a minimum and a maximum number of cells.

3. The method according to claim 1, wherein the step of dividing the cells in the cell-cell neighborhood graph into seed cells and non-seed cells comprises calculating a first metric representative of a density of the connections around a given node in the graph.

4. The method according to claim 1, wherein the step of dividing the cells in the cell-cell neighborhood graph into seed cells and non-seed cells comprises calculating a second metric representative of a neighbourhood connectedness indicating a degree of which connections are shared between many or few nodes.

5. The method according to claim 1, wherein the step of dividing the cells in the cell-cell neighborhood graph into seed cells and non-seed cells comprises selecting a least one cell from each cluster of cells, randomly or based on how central the cell is in the cluster of cells.

6. The method according to claim 1, wherein the step of clustering the cells in the cell-cell neighborhood graph converts the cell-cell neighborhood graph to a dendrogram structure, wherein each cell is represented as a leaf node and the leaves are connected to each other through branch point nodes in the dendrogram structure, wherein the step of clustering the cells in the cell-cell neighborhood graph comprises the step of ranking each cell based on how many branch point nodes that are between the cell and a root node of the dendrogram structure and clustering based on the ranking.

7. The method according to claim 1, wherein the step of clustering the cells in the cell-cell neighborhood graph converts the cell-cell neighborhood graph to a dendrogram structure, wherein each cell is represented as a leaf node and the leaves are connected to each other through branch point nodes in the dendrogram structure, wherein the step of clustering the cells in the cell-cell neighborhood graph comprises the step of partitioning the leaf nodes and branch point nodes into groups of cells, the groups having an upper bound and a lower bound.

8. The method according to claim 7, wherein the upper bound is smaller than, or equal to, 300, preferably smaller than, or equal to, 200, even more preferably smaller than, or equal to, 100.

9. The method according to claim 1, wherein the step of clustering the cells in the cell-cell neighborhood graph comprises the step of performing a first partitioning and for each partition of the first partitioning determining a number of sub-partitions based on a measure of strength of inter-connectivity of cells with each partition of the first partitioning.

10. The method according to claim 9, further comprising the step of performing sub-partitioning within the partitions of the first partitioning.

11. The method according to claim 10, wherein the step of performing sub-partitioning comprises the step of converting the cells within each partition of the first partitioning to a dendrogram structure indicating a hierarchical relationship between the cells.

12. The method according to claim 1, wherein a single first prize is higher than a single second prize, preferably wherein the second prize is 0, or wherein the at least one first prize and the at least one second prize are individually configurable prizes for the individual seed-cells and non-seed cells.

13. The method according to claim 1, further comprising the step of assigning penalties to edges between the vertices, wherein the penalties represent a degree of dissimilarity between the cells of the vertices.

14. The method according to claim 1, comprising the step of performing single-cell genomics sequencing to obtain the single-cell genomics dataset represented in at least two dimensions.

15. The method according to claim 1, comprising the step of performing a single-cell isolation.

16. The method according to claim 1, comprising the step of loading the single-cell genomics dataset represented in at least two dimensions into a digital medium of a computer system.

17. A non-transitory computer readable medium for storing computer instructions which, when executed by at least one processor causes the at least one processor to perform the method of extracting a subsample of cells from a plurality of cells in a single-cell genomics dataset according to claim 1.

18. A computer system comprising:
a memory; and
a processing unit configured to perform the steps of:
    loading a single-cell genomics dataset represented in at least two dimensions into the memory, wherein information about each cell is represented in a first dimension and information about genomic features is represented in a second dimension;
    generating a cell-cell neighborhood graph from the single-cell genomics dataset, the cell-cell neighborhood graph providing information about similarities of the genomic features of the cells, wherein the cells are represented as vertices in the cell-cell neighborhood graph, wherein the step of generating the cell-cell neighborhood graph from the single-cell genomics dataset comprises performing a k nearest neighbors algorithm, wherein the k nearest neighbors algorithm comprises identifying k nearest neighbors of each cell, wherein k is a positive integer, and creating a cell-cell neighborhood graph wherein the cells are represented as vertices and the vertices are connected via edges if at least one of the vertices is a k nearest neighbor of the other one;
    dividing the cells in the cell-cell neighborhood graph into computational seed cells and non-seed cells, wherein seed cells are selected to capture a heterogeneity of the cells;
    assigning at least one first prize to the seed cells and at least one second prize to the non-seed cells in the cell-cell neighborhood graph; and traversing the cell-cell neighborhood graph using a prize collecting steiner tree algorithm, wherein the algorithm is configured to include as many seed cells as possible and as few non-seed cells as possible, to obtain a subsample of cells.

19. The computer system according to claim 18, further comprising a display, wherein the processing unit is configured to display a graphical representation of the subsample of cells on the display.

\* \* \* \* \*